United States Patent [19]
Sugimoto et al.

[11] Patent Number: 5,876,983
[45] Date of Patent: Mar. 2, 1999

[54] MUTANT PHOSPHOENOLPYRUVATE CARBOXYLASE, ITS GENE, AND PRODUCTION METHOD OF AMINO ACID

[75] Inventors: Masakazu Sugimoto; Tomoko Suzuki; Hiroshi Matsui, all of Kawasaki; Katsura Izui, Kyoto, all of Japan

[73] Assignee: Ajinomoto Co., Inc., Tokyo, Japan

[21] Appl. No.: 596,366

[22] PCT Filed: Aug. 17, 1994

[86] PCT No.: PCT/JP94/01365

§ 371 Date: Apr. 29, 1996

§ 102(e) Date: Apr. 29, 1996

[87] PCT Pub. No.: WO95/06114

PCT Pub. Date: Mar. 2, 1995

[30] Foreign Application Priority Data

Aug. 24, 1993 [JP] Japan ................................. 5-209775
Aug. 24, 1993 [JP] Japan ................................. 5-209776
Jul. 5, 1994 [JP] Japan ................................. 6-153876

[51] Int. Cl.$^6$ ............................. C12P 13/04; C12P 13/24; C12P 13/12; C12P 13/08
[52] U.S. Cl. .......................... 435/106; 435/107; 435/110; 435/113; 435/115; 435/116; 435/232; 435/252.3; 435/252.33; 435/320.1; 536/23.1; 536/23.2; 536/23.7
[58] Field of Search ............................. 435/106, 252–33, 435/232, 107, 110, 113, 115, 116, 252.3, 320.1; 536/23.2, 23.1, 23.7

[56] References Cited

FOREIGN PATENT DOCUMENTS 0358940  3/1990  European Pat. Off. .

OTHER PUBLICATIONS

Biochem. Biophys. Res. Commun., vol. 45, No. 3, 5 Nov. 1971, pp. 689–694.
J. Biochem., vol. 81, No. 5, 1977, pp. 1473–1485.
J. Biochem., vol. 85, No. 2, Feb. 1979, pp. 423–432.
J. Biochem., vol. 84, No. 4, 1978, pp. 795–803.
Fujita et al. "The primary structure of phosphoenolpyruvate carboxylase of *Escherichia coli*. Nucleotide sequence ... " J. Biochem. 95, 909–916, 1984.

*Primary Examiner*—Robert A. Wax
*Assistant Examiner*—Nashaat T. Nashed
*Attorney, Agent, or Firm*—Oblon, Spivak, McClelland, Maier & Neustadt, P.C.

[57] ABSTRACT

A phosphoenolpyruvate carboxylase gene, which has mutation such as mutation to replace 625th glutamic acid from the N-terminus of phosphoenolpyruvate carboxylase with lysine, mutation to replace 438th arginine from the N-terminus with cysteine and the like, is introduced into *Escherichia coli* or coryneform bacteria, so as to produce a phosphoenolpyruvate carboxylase which is not substantially inhibited by aspartic acid, thereby amino acid is efficiently produced.

13 Claims, 13 Drawing Sheets

WILD TYPE ENZYME (●)　　K650A MUTANT ENZYME (○)
K491A MUTANT ENZYME (□)　K620S MUTANT ENZYME (◇)

MUTANT PHOSPHOENOLPYRUVATE CARBOXYLASE, ITS GENE, AND PRODUCTION METHOD OF AMINO ACID

TECHNICAL FIELD

The present invention relates to a mutant phosphoenolpyruvate carboxylase, a gene coding for it, and a production method of an amino acid, and in particular relates to a gene having mutation to desensitize feedback inhibition by aspartic acid, and utilization thereof.

BACKGROUND ART

Phosphoenolpyruvate carboxylase is an enzyme which is found in almost all bacteria and all plants. The role of this enzyme resides in biosynthesis of aspartic acid and glutamic acid, and supply of C4 dicarboxylic acid to the citric acid cycle for maintaining its turnover. However, in the fermentative production of an amino acid using a microorganisms, there have been few reports on effects of this enzyme has not been made clear (Atsushi Yokota and Isamu Shiio, Agric. Biol. Chem., 52, 455–463 (1988), Josef Cremer et al., Appl. Environ. Microbiol., 57, 1746–1752 (1991), Petra, G. Peters-Weintisch, FEMS Microbiol. Letters, 112, 269–274 (1993)).

By the way, the amino acid is a compound which universally exists in cells as components of proteins, however, for the sake of economic energy metabolism and substance metabolism, its production is strictly controlled. This control is principally feedback control, in which the final product of a metabolic pathway inhibits the activity of an enzyme which catalyzes the earlier step of the pathway. Phosphoenolpyruvate carboxylase also undergoes various regulations in expression of its activity.

For example, in the case of phosphoenolpyruvate carboxylase of microorganisms belonging to the genus Corynebacterium or the genus Escherichia, the activity is inhibited by aspartic acid. Therefore, the aforementioned amino acid biosynthesis, in which phosphoenolpyruvate carboxylase participates, is also inhibited by aspartic acid.

In the prior art, various techniques have been developed for efficient production in amino acid fermentation, and fermentative production has been carried out for leucine, isoleucine, tryptophan, phenylalanine and the like by using mutant strains converted to be insensitive to feedback control. However, there has been known neither mutant phosphoenolpyruvate carboxylase converted to be insensitive to inhibition by aspartic acid, nor attempt to utilize it for fermentative production of amino acids of the aspartic acid family and the glutamic acid family.

On the other hand, ppc gene, which is a gene coding for phosphoenolpyruvate carboxylase of *Escherichia coli*, has been already cloned, and also determined for its nucleotide sequence (Fujita, N., Miwa, T., Ishijima, S., Izui, K. and Katsuki, H., *J. Biochem.*, 95, 909–916 (1984)). However, there is no report of a mutant in which inhibition by aspartic acid is desensitized.

The present invention has been made from the aforementioned viewpoint, an object of which is to provide a mutant phosphoenolpyruvate carboxylase with substantially desensitized feedback inhibition by aspartic acid, a gene conding for it, and a utilization method thereof.

DISCLOSURE OF THE INVENTION

As a result of diligent investigation in order to achieve the aforementioned object, the present inventors have found that the inhibition by aspartic acid is substantially desensitized by replacing an amino acid at a specified site of phosphoenolpyruvate carboxylase of *Escherichia coli* with another amino acid, succeeded in obtaining a gene coding for such a mutant enzyme, and arrived at completion of the present invention.

Namely, the present invention lies in a mutant phosphoenolpyruvate carboxylase, which originates from a microorganism belonging to the genus Escherichia, and has mutation to desensitize feedback inhibition by aspartic acid, and a DNA sequence coding for the mutant phosphoenolpyruvate carboxylase.

The present invention further provides microorganisms belonging to the genus Escherichia or coryneform bacteria harboring the DNA fragment, and a method of producing an amino acid wherein any of these microorganisms is cultivated in a preferable medium, and the amino acid selected from L-lysine, L-threonine, L-methionine, L-isoleucine, L-glutamic acid, L-arginine and L-proline is separated from the medium.

Incidentally, in this specification, the DNA sequence coding for the mutant phosphoenolpyruvate carboxylase, or a DNA sequence containing a promoter in addition thereto is occasionally merely referred to as "DNA sequence of the present invention", "mutant gene" or "phosphoenolpyruvate carboxylase gene."

The present invention will be explained in detail hereinafter.

<1> Mutant phosphoenolpyruvate carboxylase

The mutant phosphoenolpyruvate carboxylase of the present invention (hereinafter simply referred to as "mutant enzyme") lies in the phosphoenolpyruvate carboxylase of the microorganism belonging to the genus Escherichia, which has mutation to desensitize the feedback inhibition by aspartic acid.

Such mutation may be any one provided that the aforementioned feedback inhibition is substantially desensitized without losing the enzyme activity of the phosphoenolpyruvate carboxylase, for which there may be exemplified mutation which, when a mutant phosphoenolpyruvate carboxylase having the mutation is allowed to exist in cells of a microorganism belonging to the genus Escherichia, gives the cells resistance to a compound having the following properties:

it exhibits a growth inhibitory action against a microorganism belonging to the genus Escherichia which produces a wild type phosphoenolpyruvate carboxylase;

the aforementioned growth inhibitory action is recovered by existence of L-glutamic acid or L-aspartic acid; and it inhibits wild type phosphoenolpyruvic carboxylase activity.

More concretely, there may be exemplified, as counted from the N-terminus of the phosphoenolpyruvate carboxylase:

(1) mutation to replace 625th glutamic acid with lysine;

(2) mutation to replace 222th arginine with histidine and 223th glutamic acid with lysine, respectively;

(3) mutation to replace 288th serine with phenylalanine, 289th glutamic acid with lysine, 551th methionine with isoleucine and 804th glutamic acid with lysine, respectively;

(4) mutation to replace 867th alanine with threonine;

(5) mutation to replace 438th arginine with cysteine; and (6) mutation to replace 620th lysine with serine.

Incidentally, as the phosphoenolpyruvate carboxylase of the microorganism belonging to the genus Escherichia, an amino acid sequence, which is deduced from a phosphoenolpyruvate carboxylase gene of *Escherichia coli* (Fujita, N., Miwa, T., Ishijima, S., Izui, K. and Katsuki, H., *J. Biochem.*, 95, 909–916 (1984)), is shown in SEQ ID NO:2 in the Sequence listing. In addition, an entire nucleotide sequence of a plasmid pT2, which contains the phosphoenolpyruvate carboxylase gene of *Escherichia coli*, is shown in SEQ ID NO:1 together with the amino acid sequence.

The aforementioned mutant enzymes are encoded by DNA sequences of the present invention described below, which are produced by expressing the DNA sequences in *Escherichia coli* and the like.

<2> DNA sequence of the present invention and microorganisms harboring the same

The DNA sequence of the present invention is DNA sequences coding for the aforementioned mutant enzymes, and has mutation to desensitize feedback inhibition of phosphoenolpyruvate carboxylase by aspartic acid in coding regions in DNA fragments coding for phosphoenolpyruvate carboxylase of the microorganism belonging to the genus Escherichia.

Concretely, there may be exemplified a DNA Sequence coding for the phosphoenolpyruvate carboxylase having the mutation of any one of the aforementioned (1) to (6), for example, with respect to the nucleotide sequence of SEQ ID NO:1, there may be exemplified a DNA sequence having any one of:

i) mutation to convert GAA of base Nos. 2109–2111 into AAA or AAG;

ii) mutation to convert CGC of base Nos. 900–902 into CAT or CAC, and GAA of 903–905 into AAA or AAG, respectively;

iii) mutation to convert TCT of base Nos. 1098–1100 into TTT or TTC, GAA of 1101–1103 into AAA or AAG, ATG of 1887–1889 into ATT, ATC or ATA, and GAA of 2646–2648 into AAA or AAG, respectively;

iv) mutation to convert GCG of 2835–2837 into any one of ACT, ACC, ACA and ACG; and v) mutation to convert CGT of 1548–1550 into TGT or TGC; and vi) mutation to convert AAA of 2094–2096 into TCT, TCC, TCA or TCG.

Such a mutant gene is obtained such that a recombinant DNA, which is obtained by ligating a phosphoenolpyruvate carboxylase gene as a wild type enzyme gene or having another mutation with a vector DNA adaptable to a host, is subjected to a mutation treatment, to perform screening from transformants by the recombinant DNA. Alternatively, it is also acceptable that a microorganism which produces a wild type enzyme is subjected to a mutation treatment, a mutant strain which produces a mutant enzyme is created, and then a mutant gene is screened from the mutant strain. For the mutation treatment of the recombinant DNA, hydroxylamine and the like may be used. Further, when an microorganism itself is subjected to a mutation treatment, a drug or a method usually used for artificial mutation may be used.

Further, in accordance with methods such as the Overlapping Extension method (Ho, S. N., Hunt, H. D., Horton, R. M., Pullen, J. K. and Pease, L. R., *Gene*, 77, 51–59 (1989)), the site specific mutation method (Kramer, W. and Frits, H. J., *Meth. in Enzymol.*, 154, 350 (1987); Kunkel, T. A. et al., *Meth. in Enzymol.*, 154, 367 (1987)) and the like, the aforementioned mutant gene can be also obtained by introducing mutation such as amino acid replacement, insertion, deletion and the like into a phosphoenolpyruvate carboxylase gene as a wild type enzyme gene or having another mutation. These methods are based on a principle that a non-mutated gene DNA is used as a template, and a synthetic DNA containing a mismatch at a mutation point is used as one of primers so as to synthesize complemental strands of the aforementioned gene DNA, thereby mutation is introduced. By using these methods, it is possible to cause intended mutation at an aimed site.

Alternatively, a sequence, which has restriction enzyme cleavage ends at both termini and includes both sides of a mutation point, is synthesized, and exchanged for a corresponding portion of a non-mutated gene, thereby mutation can be introduced (cassette mutation method).

The phosphoenolpyruvate carboxylase gene, which is the wild type enzyme gene or has another mutation to be used for introduction of mutation, may be any one provided that it is a gene coding for the phosphoenolpyruvate carboxylase of the microorganism belonging to the genus Escherichia, which is preferably determined for its base sequence and cloned. When it has not been cloned, a DNA fragment containing the gene can be amplified and isolated by using the PCR method and the like, followed by using a suitable vector to achieve cloning.

As the gene as described above, for example, there may be exemplified a gene of *Escherichia coli* having been cloned and determined for its base sequence (Fujita, N., Miwa, T., Ishijima, S., Izui, K. and Katsuki, H., *J. Biochem.*, 95, 909–916 (1984)). The sequence in the coding region of this gene is as shown in SEQ ID NO:1 (base Nos. 237–2888).

Screening of a host harboring the mutant gene can be performed by using an analog compound of aspartic acid. The analog compound preferably has the following properties. Namely, it exhibits a growth inhibitory action against a microorganism belonging to the genus Escherichia which produces a wild type phosphoenolpyruvate carboxylase, the aforementioned growth inhibitory action is recovered by existence of L-glutamic acid or L-aspartic acid, and it inhibits wild type phosphoenolpyruvate carboxylase activity.

If a mutant strain beeing resistant to the analog compound mentioned above is selected from microorganism belonging to the genus Escherichia, for example, *Escherichia coli* HB101 producing wild type phosphoenolpyruvate carboxylase using inhibition of growth of the microorganism as an index, it is much likely to obtain a host microorganism which produces phosphoenolpyruvate carboxylase with desensitized feedback inhibition by aspartic acid.

It is proposed, as a general structure of an inhibitor of phosphoenolpyruvate carboxylase, that a C4 dicarboxylic acid structure is essentially provided. From such a viewpoint, various compounds were subjected to screening by the present inventors. *Escherichia coli* HB101 was cultivated in an LB medium, and transferred to M9 media (containing 20 µg/ml of thiamine and 3 µg/ml of each of Leu and Pro) containing any one of DL-2-amino-4-phosphonobutyric acid, bromosuccinic acid, meso-2,3-dibromosuccinic acid, 2,2-difluorosuccinic acid, 3-bromopyruvic acid, α-ketobutyric acid, α-ketoadipinic acid, DL-threo-β-hydroxyaspartic acids L-aspartic acid-β-metyl ester, α-metyl-DL-aspartic acid, 2,3-diaminosuccinic acid or aspartic acid-β-hydrazide, and absorbance of the medium was measured at 660 nm with the passage of time, thereby growth was monitored.

Further, when these compounds were present at their growth inhibitory concentrations, it was investigated whether or not the inhibition was recovered by addition of nucleic acids (each of uridine, adenosine: 10 mg/dl), glutamic acid or amino acids of the aspartic acid family (Asp: 0.025%, each of Met, Thr, Lys: 0.1%).

As a result, three compounds: 3-bromopyruvate (3BP) (1), aspartate-β-hydrazide (AHY) (2), and DL-threoβ-hydroxyaspartate (βHA) (3) were selected.

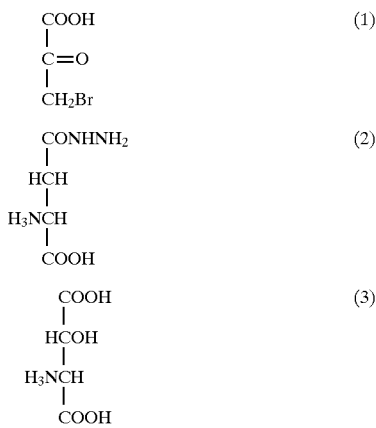

Growth inhibition of *Escherichia coli* by these analog compounds is shown in FIGS. 1–3. Further, growth recovery of *Escherichia coli*, in the case of addition of the aforementioned inhibition recovering substances alone or as a mixture of 2 species or 3 species, is shown in FIGS. 4–6. In addition, as a control, growth in the case of addition of the inhibition recovering substance in the absence of the inhibitory substance is shown in FIG. 7. Incidentally, in FIGS. 4–7, additives 1, 2 and 3 indicate nucleic acids, glutamic acid or amino acids of the aspartic acid family, respectively.

Further, inhibition of activity by the analog compound on phosphoenolpyruvate carboxylase was investigated. Crude enzyme was prepared from an *Escherichia coli* HB101 strain in accordance with a method described in *The Journal of Biochemistry*, Vol. 67, No. 4 (1970), and enzyme activity was measured in accordance with a method described in *Eur. J. Biochem.*, 202, 797–803 (1991).

*Escherichia coli* HB101 cultivated in an LB medium was disrupted, and a suspension was centrifuged to obtain a supernatant which was used as a crude enzyme solution. Measurement of enzyme activity was performed by measuring decrease in absorbance at 340 nm while allowing acetyl-coenzyme A known to affect the activity to exist at a concentration of 0.1 mM in a measurement system containing 2 mM potassium phosphoenolpyruvate, 0.1 mM NADH, 0.1M Tris-acetate (pH 8.5), 1.5 U malate dehydrogenase and crude enzyme. Results are shown in FIG. 8.

According to the results as above, it is apparent that the aforementioned three compounds inhibit growth of *Escherichia coli*, this inhibition cannot be recovered by nucleic acids alone, but the inhibition can be recovered by addition of glutamic acid or amino acids of the aspartic acid family. Therefore, these analog compounds were postulated to be selective inhibitors of phosphoenolpyruvate carboxylase. As shown in Examples described below, by using these compounds, the present invention has succeeded in selection of an *Escherichia coli* which produces the mutant phosphoenolpyruvate carboxylase.

When a transformant having an aimed mutant enzyme gene is screened by using the aforementioned compounds, and a recombinant DNA is recovered, then the mutant enzyme gene is obtained. Alternatively, in the case of a mutation treatment of an microorganism itself, when a mutant strain having an aimed mutant enzyme gene is screened by using the aforementioned compounds, a DNA fragment containing the aimed mutant enzyme gene is isolated from the strain, and it is ligated with a suitable vector, then the mutant enzyme gene is obtained.

On the other hand, as a result of diligent investigation by the present inventors taking notice of importance of an arginine residue in an aspartate binding protein of *Escherichia coli* (Krikos, A., Mouth, N., Boyd, A. and Simon, M. I. *Cell*, 33, 615–622 (1983), Mowbray, S. L and Koshland, D. E. *J. Biol. Chem.*, 264, 15638–15643 (1990), Milburn, M. V., Prive, G. G., Milligan, D. L., Scott, W. G., Yeh, J., Jancarik, J., Koshland, D. E. and Kim, S. H., *Science*, 254, 1342–1347 (1991)), it has been found that inhibition by aspartic acid is substantially desensitized by converting 438th arginine of phosphoenolpyruvate carboxylase into cysteine. In order to convert 438th arginine into cysteine, a codon of 438th arginine of a gene coding for phosphoenolpyruvate carboxylase may be converted into a codon of cysteine. For example, in SEQ ID NO:1, CGT of nucleotide numbers of 1548–1550 may be converted into TGT or TGC.

Further, the present inventors performed chemical modification of lysine residues of phosphoenolpyruvate carboxylase by using 2,4,6-trinitrobenzenesulfonic acid (TNBS) which is a compound to chemically modify lysine residues of a protein. During modification reaction, malic acid capable of serving as an inhibitor of phosphoenolpyruvate carboxylase was allowed to exist together. Namely, it was assumed that a lysine residue in the vicinity of a binding position of phosphoenolpyruvate carboxylase would be protected by bound malic acid and not be subjected to chemical modification. As a result, it was suggested that a 620th lysine residue was important for malic acid to bind phosphoenolpyruvate carboxylase, and it was found that the feedback inhibition by aspartic acid was desensitized while maintaining the enzyme activity of phosphoenolpyruvate carboxylase by converting the 620th lysine residue into a serine residue. In order to convert the 620th lysine residue into the serine residue, a codon of 620th lysine of the gene coding for phosphoenolpyruvate carboxylase may be converted into a codon of serine. For example, in SEQ ID NO:1, AAA having nucleotide numbers of 2094–2096 may be replaced with TCT, TCC, TCA, TCG, AGT or AGC.

In accordance with methods such as the Overlapping Extension method (Ho, S. N., Hunt, H. D., Horton, R. M., Pullen, J. K. and Pease, L. R., *Gene*, 77, 51–59 (1989)), the site specific mutation method (Kramer, W. and Frits, H. J., *Meth. in Enzymol.*, 154, 350 (1987); Kunkel, T. A. et al., *Meth. in Enzymol.*, 154, 367 (1987)) and the like, conversion of the codon can be also achieved by introducing mutation such as amino acid replacement, insertion, deletion and the like into a phosphoenolpyruvate carboxylase gene as a wild type enzyme gene or having another mutation. These methods are based on a principle that a non-mutated gene DNA is used as a template, and a synthetic DNA containing a mismatch at a mutation point is used as one of primers so as to synthesize complemental strands of the aforementioned gene DNA, thereby mutation is introduced. By using these methods, it is possible to cause intended mutation at an aimed site.

Alternatively, a sequence, which has restriction enzyme cleavage ends at both termini and contains both sides of a mutation point, is synthesized, and exchanged for a corresponding portion of a non-mutated gene, thereby mutation can be introduced (cassette mutation method).

The DNA fragment coding for the phosphoenolpyruvate carboxylase with mutation introduced as described above is expressed by using a suitable host-vector system, thereby it is possible to produce a mutant enzyme. Alternatively, even by performing transformation by integrating the DNA fragment of the present invention into a host chromosomal DNA, an aimed mutant enzyme can be produced.

As the host, there may be exemplified microorganisms belonging to the genus Escherichia, for example, *Escherichia coli*, coryneform bacteria and the like. The coryneform bacteria include bacteria belonging to the genus Corynebacterium, bacteria belonging to the genus Brevibacterium having been hitherto classified into the genus Brevibacterium but being united as bacteria belonging to the genus Corynebacterium at present, and bacteria belonging to the genus Brevibacterium closely related to bacteria belonging to the genus Corynebacterium. Incidentally, hosts which are preferable for amino acid production will be described below.

On the other hand, as the vector DNA, a plasmid vector is preferable, and those capable of self-replication in a host cell are preferable. When the host is *Escherichia coli*, for example, pUC19, pUC18, pBR322, pHSG299, pHSG399, RSF1010 and the like are exemplified. Alternatively, a vector of phage DNA can be also utilized.

Further, when the host is the coryneform bacteria, vectors which can be used and hosts which harbor them are exemplified below. Incidentally, deposition numbers of international depositories are shown in parentheses.

pAJ655 *Escherichia coli* AJ11882 (FERM BP-136)
  *Corynebacterium glutamicum* SR8201 (ATCC 39135)
pAJ1844 *Escherichia coli* AJ11883 (FERM BP-137)
  *Corynebacterium glutamicum* SR8202 (ATCC 39136)
pAJ611 *Escherichia coli* AJ11884 (FERM BP-138)
pAJ3148 *Corynebacterium glutamicum* SR8203 (ATCC 39137)
pAJ440 *Bacillus subtilis* AJ11901 (FERM BP-140)

These vectors may be obtained from the deposited microorganisms as follows. Cells collected at the logarithmic growth phase are subjected to bacteriolysis by using lysozyme and SDS, and centrifuged at 30000×g to obtain a supernatant solution from a lysate, to which polyethylene glycol is added to perform separation and purification of the vectors by means of cesium chloride-ethidium bromide equilibrium density gradient centrifugation.

In order to transform *Escherichia coli* with a recombinant vector obtained by inserting the DNA sequence of the present invention into the aforementioned vector, it is possible to use a method usually used for transformation of *Escherichia coli*, such as a method in which cells are treated with calcium chloride to enhance permeability of DNA (Mandel, M. and Higa, A., *J. Mol. Biol.*, 53, 159 (1977)) and the like.

Further, as a method for transforming the coryneform bacteria, there is the aforementioned method in which cells are treated with calcium chloride, or a method in which incorporation is performed at a specified growth period in which cells can incorporate DNA (report in relation to *Bacillus subtilis* by Duncan, C. H. at al.). Further, incorporation into bacterial cells can be achieved by forming protoplasts or spheroplasts of DNA recipients which easily incorporate plasmid DNA. These are known for *Bacillus subtilis*, Actinomyces and yeast (Chang, S. et al., *Molec. Gen. Genet.*, 168, 111 (1979), Bibb et al., *Nature*, 274, 398 (1978), Hinnen, A. et al., *Proc. Natl. Acad. Sci. USA*, 75 1929 (1978)). Additionally, a method for transforming coryneform bacteria is disclosed in Japanese Patent Laid-open No. 2-207791.

In order to express the DNA sequence of the present invention in the aforementioned hosts, a promoter such as lac, trp, PL and the like which efficiently works in microorganisms may be used, or when the DNA sequence of the present invention contains a promoter of the phosphoenolpyruvate carboxylase gene, it may be used as it is. Alternatively, when the coryneform bacterium is used as the host, it is also possible to use a known trp promoter originating from a bacterium belonging to the genus Brevibacterium (Japanese Patent Laid-open No. 62-244382) and the like.

Further, as described above, it is acceptable that the DNA sequence of the present invention is inserted into the vector DNA capable of self-replication and introduced into the host to allow the host to harbor it as a plasmid, and it is also acceptable that the DNA sequence of the present invention is integrated into a chromosome of an microorganism by means of a method using transposon (Berg, D. E. and Berg, C. M., *Bio/Technol.*, 1, 417 (1983)), Mu phage (Japanese Patent Laid-open No. 2-109985) or homologous recombination (*Experiments in Molecular Genetics*, Cold Spring Harbor Lab. (1972)). In addition, in order to integrate the DNA of the present invention into the coryneform bacteria, it is possible to utilize a temperature-sensitive plasmid disclosed in Japanese Patent Laid-open No. 5-7491.

When the microorganism transformed with the DNA sequence of the present invention as described above is cultivated, and this DNA sequence is expressed, then a mutant enzyme is obtained. It becomes apparent, by measuring the activity by adding aspartic acid to an enzyme reaction system, whether or not the mutant enzyme thus obtained has desensitized feedback inhibition by aspartic acid. It is possible for the measurement of the enzyme activity to use a spectrometric method (Yoshinage, T., Izui, K. and Katsuki, H., *J. Biochem.*, 68, 747–750 (1970)) and the like.

Further, the DNA sequence of the present invention codes for the mutant enzyme in which feedback inhibition by aspartic acid is desensitized, so that the microorganism harboring this DNA sequence can be utilized for efficient fermentative production of amino acids of the aspartic acid family and the glutamic acid family as described below.

*Escherichia coli* AJ12907, AJ12908, AJ12909 and AJ12910 harboring the mutant enzyme genes obtained in Examples described below are deposited in National Institute of Bioscience and Human Technology of Agency of Industrial Science and Technology (1-3, Higashi 1-chome, Tsukuba-shi, Ibaraki-ken, Japan; zip code 305) on Aug. 3, 1993 under the deposition numbers of FERM P-13774, FERM P-13775, FERM P-13776 and FERM P-13777, transferred from the original deposition to international deposition based on Budapest Treaty on Jul. 11, 1994 and has been deposited as deposition numbers of FERM BP-4734, FERM BP-4735, FERM BP-4736, FERM BP-4737, respectively in this order.

<3> Production method of amino acids

Amino acids can be produced by cultivating the microorganism harboring the DNA sequence of the present invention in a preferable medium, and separating generated amino acids. As such amino acids, there may be exemplified L-lysine, L-threonine, L-methionine, L-isoleucine, L-glutamic acid, L-arginine and L-proline.

Preferable hosts into which the DNA sequence of the present invention is introduced to be used for production of each of the amino acids, and a cultivation method will be exemplified below.

(1) Hosts preferable for the amino acid production method of the present invention (i) Hosts preferable for L-lysine production As the host to be used for L-lysine production according to the present invention, there may be exemplified bacteria belonging to the genus Escherichia, preferably L-lysine-producing *Escherichia coli*. Concretely, a mutant strain having resistance to a lysine analog can be exemplified. Such a lysine analog is those which inhibit growth of microorganisms belonging to the genus Escherichia, however, the suppression is totally or partially desensitized provided that L-lysine co-exits in the medium. For example, there are oxalysine, lysine hydroxamate, S-(2-aminoethyl)-cysteine (hereinafter abbreviated as "AEC"), γ-methyllysine, α-chlorocaprolactam and the like. Mutant strains having resistance to these lysine analogs can be obtained by applying an ordinary artificial mutation treatment to microorganisms belonging to the genus Escherichia. Concretely, as a bacterial strain to be used for L-lysine production, there may be exemplified *Escherichia coli* AJ11442 (deposited as FERM P-5084, see lower-left column on page 471 in Japanese Patent Laid-open No. 56-18596).

On the other hand, various artificial mutant strains of coryneform bacteria which have been used as L-lysine-producing bacteria can be used for the present invention. Such artificial mutant strains are as follows: AEC resistant mutant strain; mutant strain which requires amino acid such as L-homoserine for its growth (Japanese Patent Publication Nos. 48-28078 and 56-6499); mutant strain which exhibits resistance to AEC and requires amino acid such as L-leucine, L-homoserine, L-proline, L-serine, L-arginine, L-alanine, L-valine and the like (U.S. Pat. Nos. 3,708,395 and 3,825,472); L-lysine-producing mutant strain which exhibits resistance to DL-α-amino-ε-caprolactam, α-amino-lauryllactam, quinoid and N-lauroylleucine; L-lysine-producing mutant strain which exhibits resistance to an inhibitor of oxaloacetate decarboxylase or respiratory system enzyme (Japanese Patent Laid-open Nos. 50-53588, 50-31093, 52-102498, 53-86089, 55-9783, 55-9759, 56-32995 and 56-39778, and Japanese Patent Publication Nos. 53-43591 and 53-1833); L-lysine-producing mutant strain which requires inositol or acetic acid (Japanese Patent Laid-open Nos. 55-9784 and 56-8692); L-lysine-producing mutant strain which exhibits sensitivity to fluoropyruvate or temperature not less than 34° C. (Japanese Patent Laid-open Nos. 55-9783 and 53-86090); and mutant strain of Brevibacterium or Corynebacterium which exhibits resistance to ethylene glycol and produces L-lysine (see U.S. Pat. application Ser. No. 333,455).

Followings are exemplified as concrete coryneform bacteria to be used for lysine production:

*Brevibacterium lactofermentum* AJ12031 (FERM-BP277), see page 525 in Japanese Patent Laid-open No. 60-62994;

*Brevibacterium lactofermentum* ATCC 39134, see lower-right column on page 473 in Japanese Patent Laid-open No. 60-62994;

*Brevibacterium lactofermentum* AJ3463 (FERM-P1987), see Japanese Patent Publication No. 51-34477.

In addition, wild strains of coryneform bacteria described below can be also used for the present invention in the same manner.

*Corynebacterium acetoacidophilum* ATCC 13870
*Corynebacterium acetoglutamicum* ATCC 15806
*Corynebacterium callunae* ATCC 15991
*Corynebacterium glutamicum* ATCC 13032
  ATCC 13060
(*Brevibacterium divaricatum*) ATCC 14020
(*Brevibacterium lactofermentum*) ATCC 13869
(*Corynebacterium lilium*) ATCC 15990
*Corynebacterium melassecola* ATCC 17965
*Brevibacterium saccharolyticum* ATCC 14066
*Brevibacterium immariophilum* ATCC 14068
*Brevibacterium roseum* ATCC 13825
*Brevibacterium flavum* ATCC 13826
*Brevibacterium thiogenitalis* ATCC 19240
*Microbacterium ammoniaphilum* ATCC 15354

(ii) Hosts preferable for L-threonine production

*Escherichia coli* B-3996 (RIA 1867), see Japanese Patent Laid-open No. 3-501682 (PCT);

*Escherichia coli* AJ12349 (FERM-P9574), see upper-left column on page 887 in Japanese Patent Laid-open No. 2-458;

*Escherichia coli* AJ12351 (FERM-P9576), see lower-right column on page 887 in Japanese Patent Laid-open No. 2-458;

*Escherichia coli* AJ12352 (FERM P-9577), see upper-left column on page 888 in Japanese Patent Laid-open No. 2-458;

*Escherichia coli* AJ11332 (FERM P-4898), see upper-left column on page 889 in Japanese Patent Laid-open No. 2-458;

*Escherichia coli* AJ12350 (FERM P-9575), see upper-left column on page 889 in Japanese Patent Laid-open No. 2-458;

*Escherichia coli* AJ12353 (FERM P-9578), see upper-right column on page 889 in Japanese Patent Laid-open No. 2-458;

*Escherichia coli* AJ12358 (FERM P-9764), see upper-left column on page 890 in Japanese Patent Laid-open No. 2-458;

*Escherichia coli* AJ12359 (FERM P-9765), see upper-left column on page 890 in Japanese Patent Laid-open No. 2-458;

*Escherichia coli* AJ11334 (FERM P-4900), see column 6 on page 201 in Japanese Patent Publication No. 1-29559;

*Escherichia coli* AJ11333 (FERM P-4899), see column 6 on page 201 in Japanese Patent Publication No. 1-29559;

*Escherichia coli* AJ11335 (FERM P-4901), see column 7 on page 202 in Japanese Patent Publication No. 1-29559.

Following bacterial strains are exemplified as the coryneform bacteria:

*Brevibacterium lactofermentum* AJ11188 (FERM P-4190), see upper-right column on page 473 in Japanese Patent Laid-open No. 60-87788;

*Corynebacterium glutamicum* AJ11682 (FERM BP-118), see column 8 on page 230 in Japanese Patent Publication No. 2-31956;

*Brevibacterium flavum* AJ11683 (FERM BP-119), see column 10 on page 231 in Japanese Patent Publication No. 2-31956.

(iii) Hosts preferable for L-methionine production

Following bacterial strains are exemplified for L-methionine production:

*Escherichia coli* AJ11457 (FERM P-5175), see upper-right column on page 552 in Japanese Patent Laid-open No. 56-35992;

*Escherichia coli* AJ11458 (FERM P-5176), see upper-right column on page 552 in Japanese Patent Laid-open No. 56-35992;

*Escherichia coli* AJ11459 (FERM P-5177), see upper-right column on page 552 in Japanese Patent Laid-open No. 56-35992;

*Escherichia coli* AJ11539 (FERM P-5479), see lower-left column on page 435 in Japanese Patent Laid-open No. 56-144092;

*Escherichia coli* AJ11540 (FERM P-5480), see lower-left column on page 435 in Japanese Patent Laid-open No. 56-144092;

*Escherichia coli* AJ11541 (FERM P-5481), see lower-left column on page 435 in Japanese Patent Laid-open No. 56-144092;

*Escherichia coli* AJ11542 (FERM P-5482), see lower-left column on page 435 in Japanese Patent Laid-open No. 56-144092.

(iv) Hosts preferable for L-aspartic acid production

Following bacterial strains are exemplified for L-aspartic acid production:

*Brevibacterium flavum* AJ3859 (FERM P-2799), see upper-left column on page 524 in Japanese Patent Laid-open No. 51-61689;

*Brevibacterium lactofermentum* AJ3860 (FERM P-2800), see upper-left column on page 524 in Japanese Patent Laid-open No. 51-61689;

*Corynebacterium acetoacidophilum* AJ3877 (FERM-P2803), see upper-left column on page 524 in Japanese Patent Laid-open No. 51-61689;

*Corynebacterium glutamicum* AJ3876 (FERM P-2802), see upper-left column on page 524 in Japanese Patent Laid-open No. 51-61689.

(v) Hosts preferable for L-isoleucine production

*Escherichia coli* KX141 (VKPM-B4781) (see 45th paragraph in Japanese Patent Laid-open No. 4-33027) is exemplified as the bacteria belonging to the genus Escherichia, and *Brevibacterium lactofermentum* AJ12404 (FERM P-10141) (see lower-left column on page 603 in Japanese Patent Laid-open No. 2-42988) and *Brevibacterium flavum* AJ12405 (FERM P-10142) (see lower-left column on page 524 in Japanese Patent Laid-open No. 2-42988) are exemplified as the coryneform bacteria.

(vi) Hosts preferable for L-glutamic acid production

Following bacterial strains are exemplified as the bacteria belonging to the genus Escherichia:

*Escherichia coli* AJ12628 (FERM P-12380), see French Patent Publication No. 2 680 178 (1993);

*Escherichia coli* AJ12624 (FERM P-12379), see French Patent Publication No. 2 680 178 (1993).

Following bacterial strains are exemplified as the coryneform bacteria:

*Brevibacterium lactofermentum* AJ12745 (FERM BP-2922), see lower-right column on page 561 in Japanese Patent Laid-open No. 3-49690;

*Brevibacterium lactofermentum* AJ12746 (FERM BP-2923), see upper-left column on page 562 in Japanese Patent Laid-open No. 3-49690;

*Brevibacterium lactofermentum* AJ12747 (FERM BP-2924), see upper-left column on page 562 in Japanese Patent Laid-open No. 3-49690;

*Brevibacterium lactofermentum* AJ12748 (FERM BP-2925), see upper-left column on page 562 in Japanese Patent Laid-open No. 3-49690;

*Brevibacterium flavum* ATCC 14067, see Table 1 on page 3 in Japanese Patent Laid-open No. 5-3793;

*Corynebacterium glutamicum* ATCC 21492, see Table 1 on page 3 in Japanese Patent Laid-open No. 5-3793.

(vii) Hosts preferable for L-arginine production

Following bacterial strains are exemplified as the bacteria belonging to the genus Escherichia:

*Escherichia coli* AJ11593 (FERM P-5616), see upper-left column on page 468 in Japanese Patent Laid-open No. 57-5693;

*Escherichia coli* AJ11594 (FERM P-5617), see upper-right column on page 468 in Japanese Patent Laid-open No. 57-5693.

Following bacterial strains are exemplified as the coryneform bacteria:

*Brevibacterium flavum* AJ12144 (FERM P-7642), see column 4 on page 174 in Japanese Patent Publication No. 5-27388;

*Corynebacterium glutamicum* AJ12145 (FERM P-7643), see column 4 on page 174 in Japanese Patent Publication No. 5-27388;

*Brevibacterium flavum* ATCC 21493, see Table 1 on page 3 in Japanese Patent Laid-open No. 5-3793;

*Corynebacterium glutamicum* ATCC 21659, see Table 1 on page 3 in Japanese Patent Laid-open No. 5-3793.

(viii) Hosts preferable for L-proline production

Following bacterial strains are exemplified as the bacteria belonging to the genus Escherichia:

*Escherichia coli* AJ11543 (FERM P-5483), see lower-left column on page 435 in Japanese Patent Laid-open No. 56-144093;

*Escherichia coli* AJ11544 (FERM P-5484), see lower-left column on page 435 in Japanese Patent Laid-open No. 56-144093.

Following bacterial strains are exemplified as the coryneform bacteria:

*Brevibacterium lactofermentum* AJ11225 (FERM P-4370), see upper-left column on page 473 in Japanese Patent Laid-open No. 60-87788;

*Brevibacterium flavum* AJ11512 (FERM P-5332), see column 2 on page 185 in Japanese Patent Publication No. 62-36679;

*Brevibacterium flavum* AJ11513 (FERM P-5333), see column 2 on page 185 in Japanese Patent Publication No. 62-36679;

*Brevibacterium flavum* AJ11514 (FERM P-5334), see column 2 on page 185 in Japanese Patent Publication No. 62-36679;

*Corynebacterium glutamicum* AJ11522 (FERM P-5342), see column 2 on page 185 in Japanese Patent Publication No. 62-36679;

*Corynebacterium glutamicum* AJ11523 (FERM P-5343), see column 2 on page 185 in Japanese Patent Publication No. 62-36679.

(2) Cultivation method

The method for cultivating the aforementioned hosts is not especially different from a cultivation method for amino acid-producing microorganisms in the prior art. Namely, an ordinary medium is used containing a carbon source, a nitrogen source and inorganic ions, and optionally organic trace nutrients such as amino acids, vitamins and the like.

As the carbon source, glucose, sucrose, lactose and the like, as well as starch hydrolysate, whey, molasses and the like containing them may be used. As the nitrogen source, ammonia gas, aqueous ammonium, ammonium salt and the like can be used. Incidentally, when a nutrient requiring mutant strain for amino acids or the like is used as the host, it is necessary to suitably add the nutrient such as amino acid or the like required by the strain to the medium. An example of the medium for lysine production is shown in Table 1 below as a medium to be used for amino acid production. Incidentally, calcium carbonate is added to other components after being separately sterilized.

TABLE 1

| Medium component | Blending amount |
|---|---|
| glucose | 5 g/dl |
| $(NH_4)_2SO_4$ | 2.5 g/dl |
| $KH_2PO_4$ | 0.2 g/dl |
| $MgSO_4.7H_2O$ | 0.1 g/dl |
| yeast extract | 0.05 g/dl |
| thiamine hydrochloride | 1 µg/l |
| biotin | 300 µg/l |
| $FeSO_4.7H_2O$ | 1 mg/dl |
| $MnSO_4.4H_2O$ | 1 mg/dl |
| calcium carbonate | 2.5 g/dl |
| (pH 7.0) | |

The cultivation is performed until generation and accumulation of amino acids substantially stop while suitably controlling pH and temperature of the medium under an aerobic condition. In order to collect amino acids thus accumulated in the cultivated medium, an ordinary method can be applied.

BEST MODE FOR CARRYING OUT THE INVENTION

Figure 1:
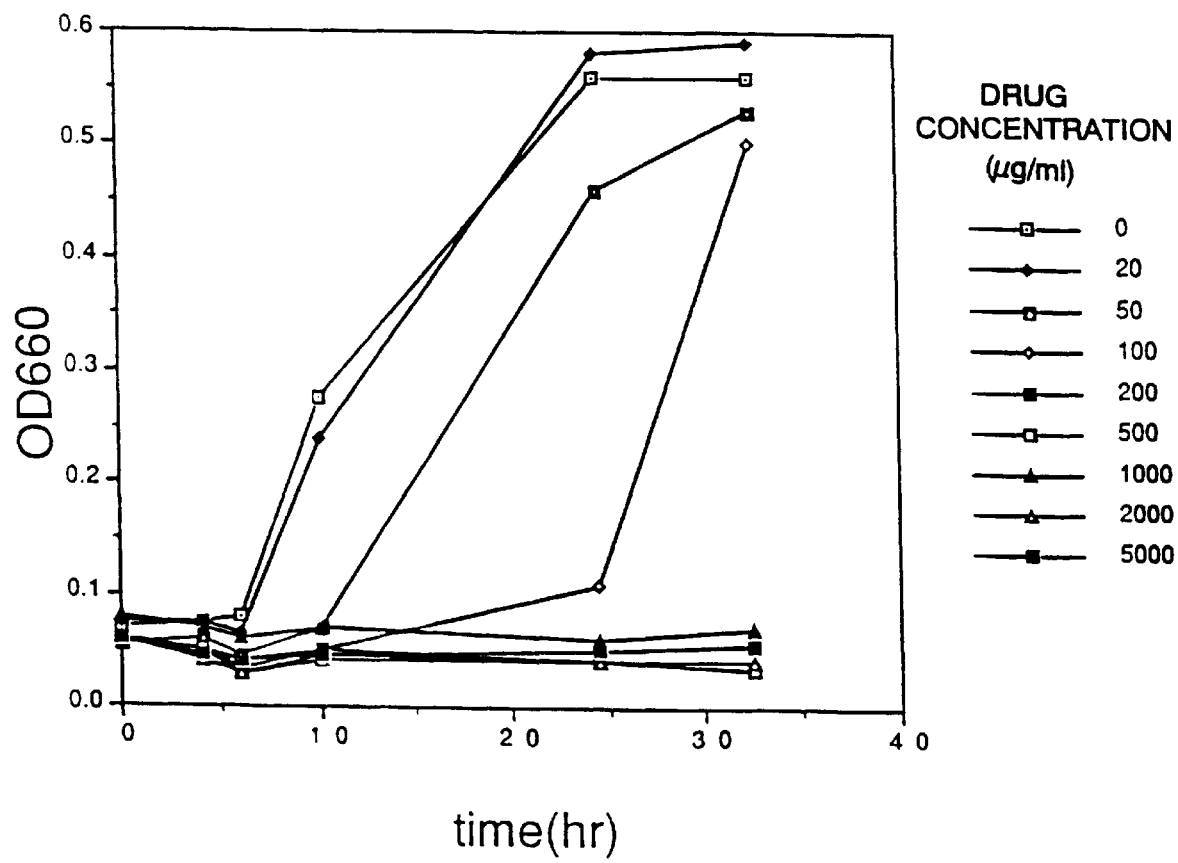
FIG. 1 shows growth inhibition by 3-bromopyruvate.
Figure 2:
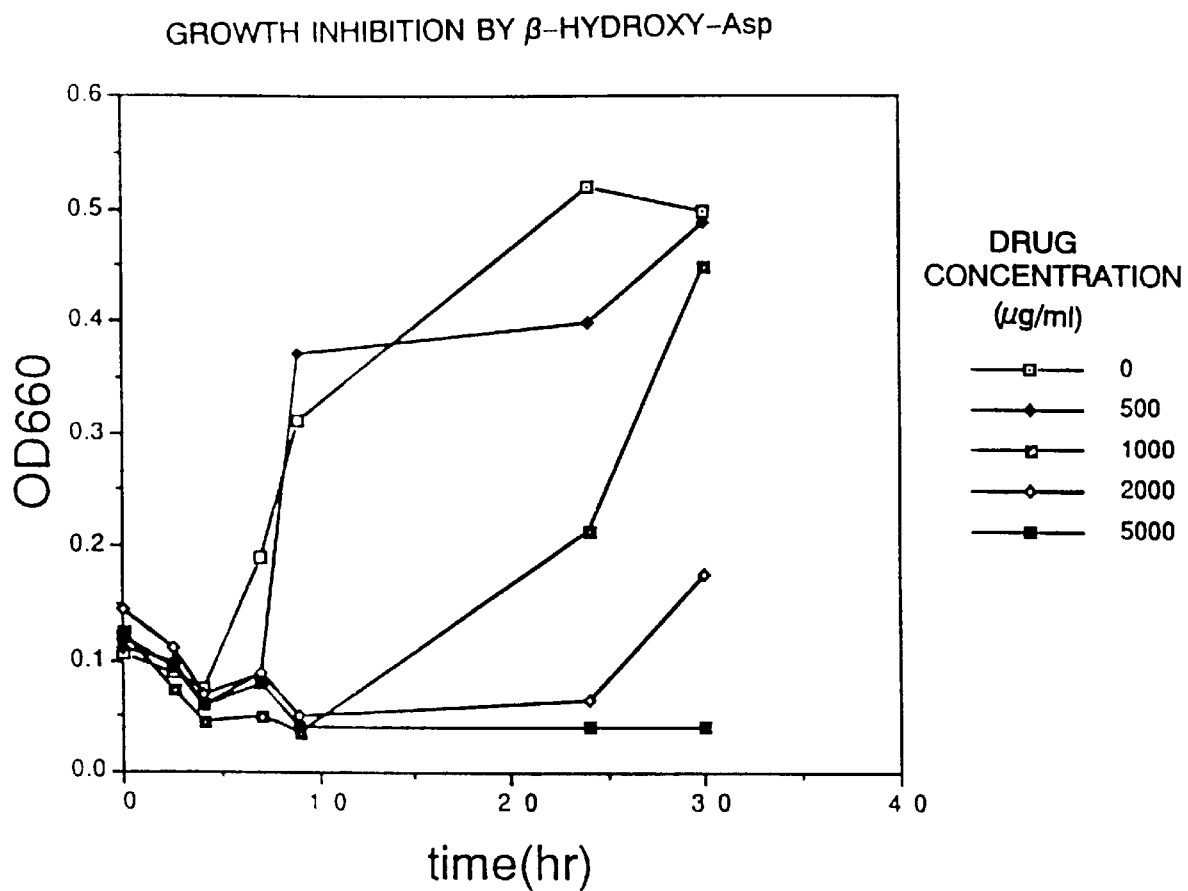
FIG. 2 shows growth inhibition by aspartate-β-hydrazide.
Figure 3:
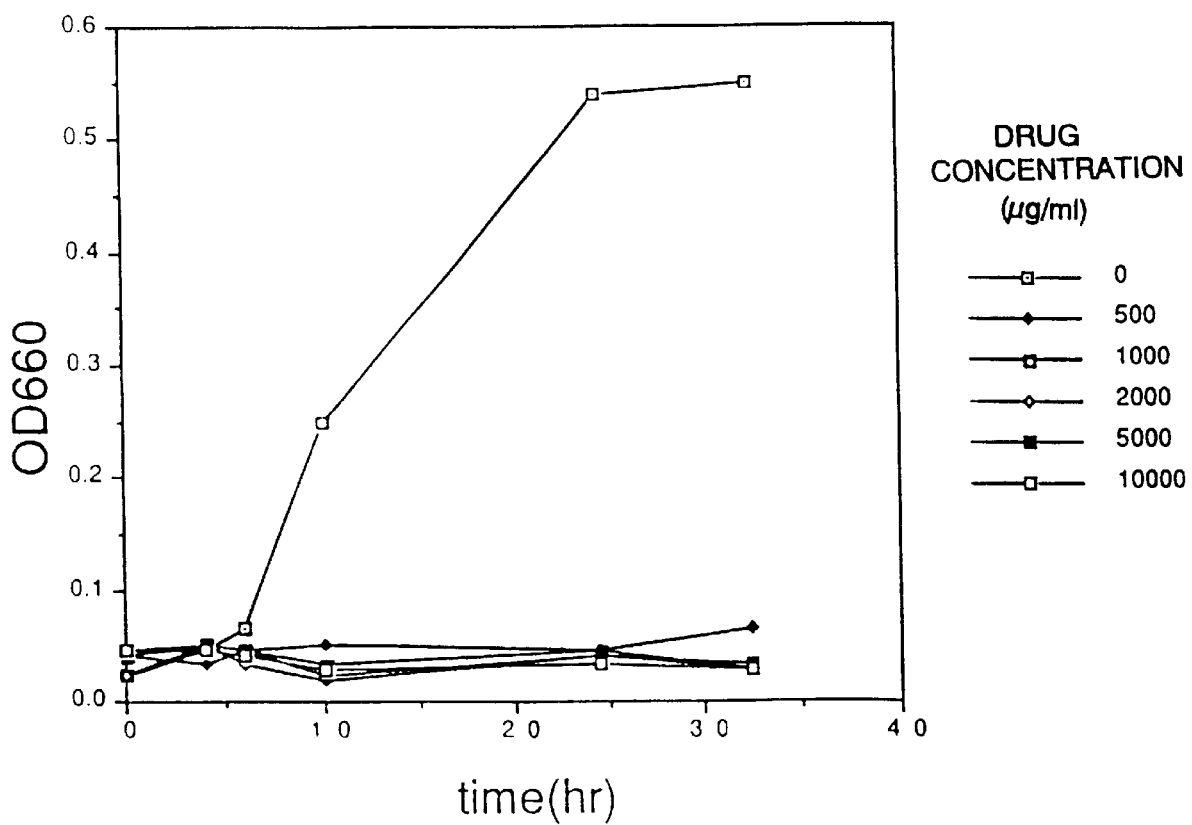
FIG. 3 shows growth inhibition by DL-threo-β-hydroxyaspartate.
Figure 4:
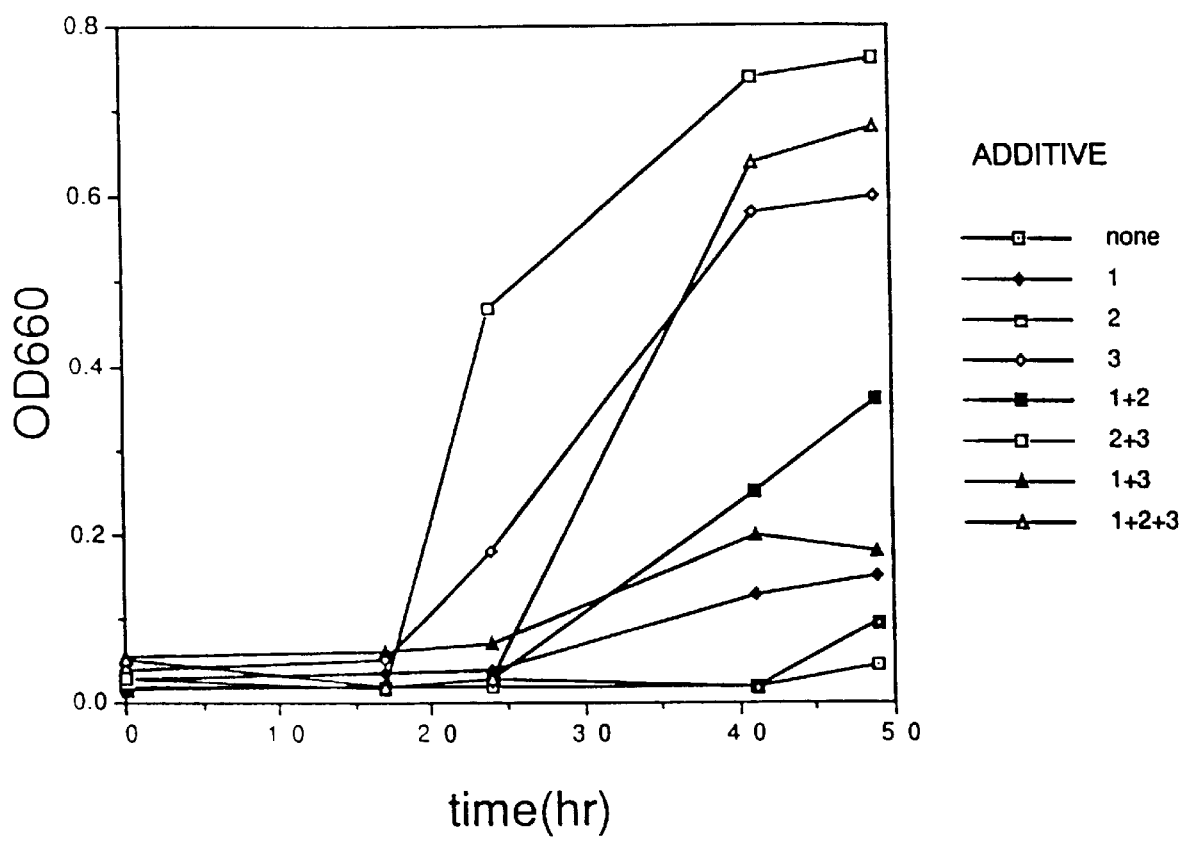
FIG. 4 shows effects of inhibition recovering substances on 3-bromopyruvate.
Figure 5:
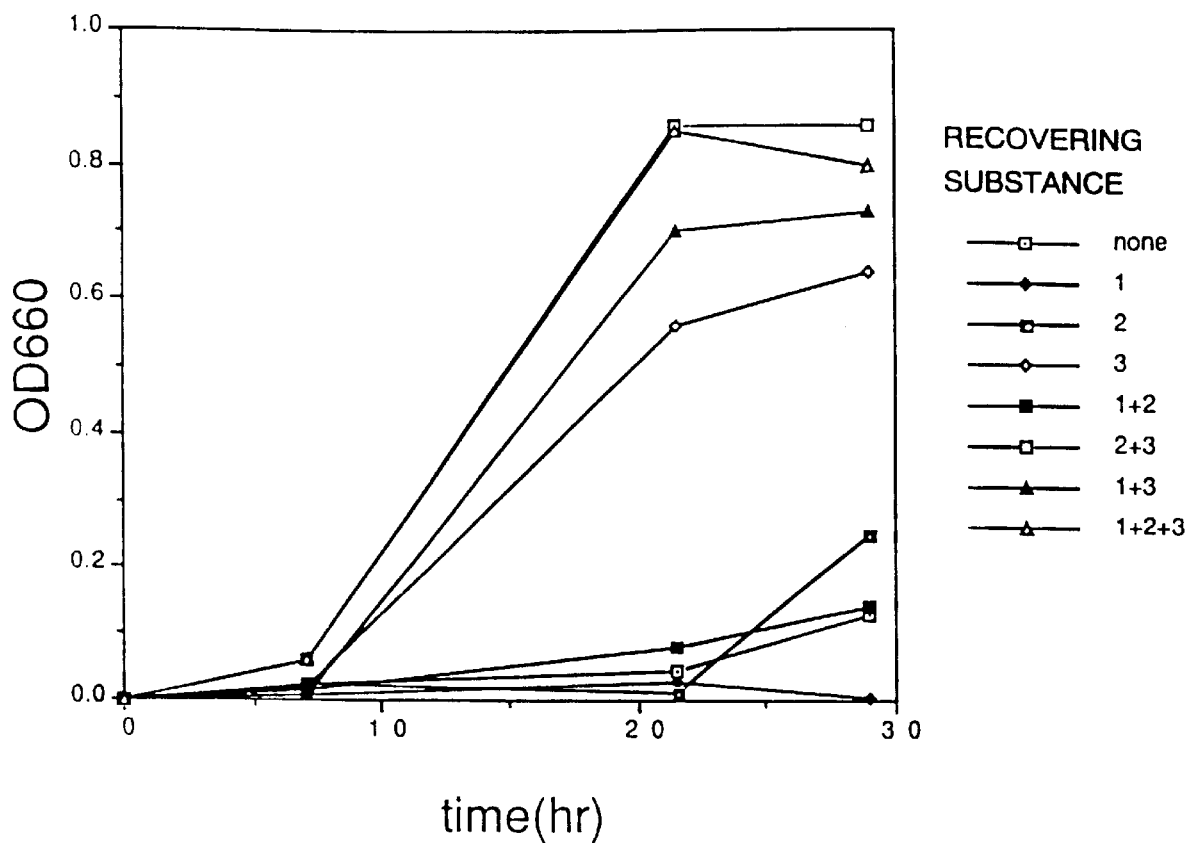
FIG. 5 shows effects of inhibition recovering substances on aspartate-β-hydrazide.
Figure 6:
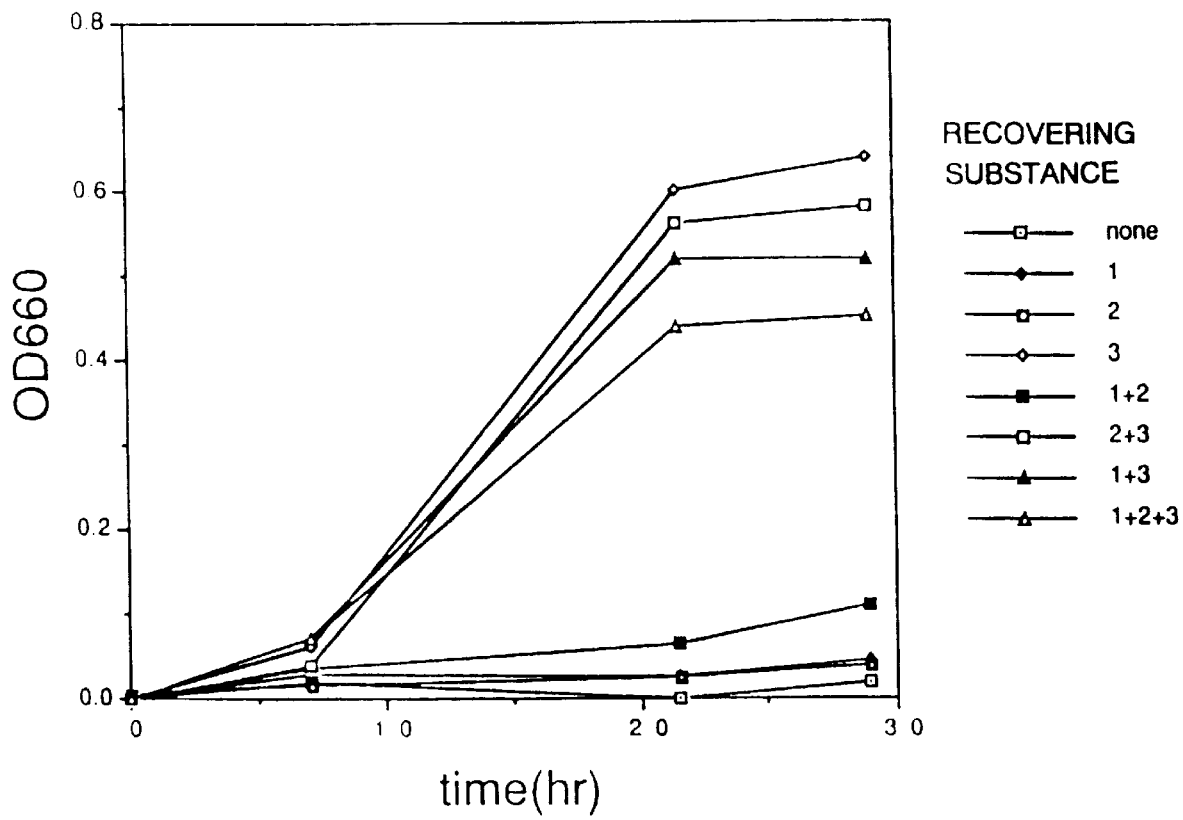
FIG. 6 shows effects of inhibition recovering substances on DL-threo-β-hydroxyaspartate.
Figure 7:
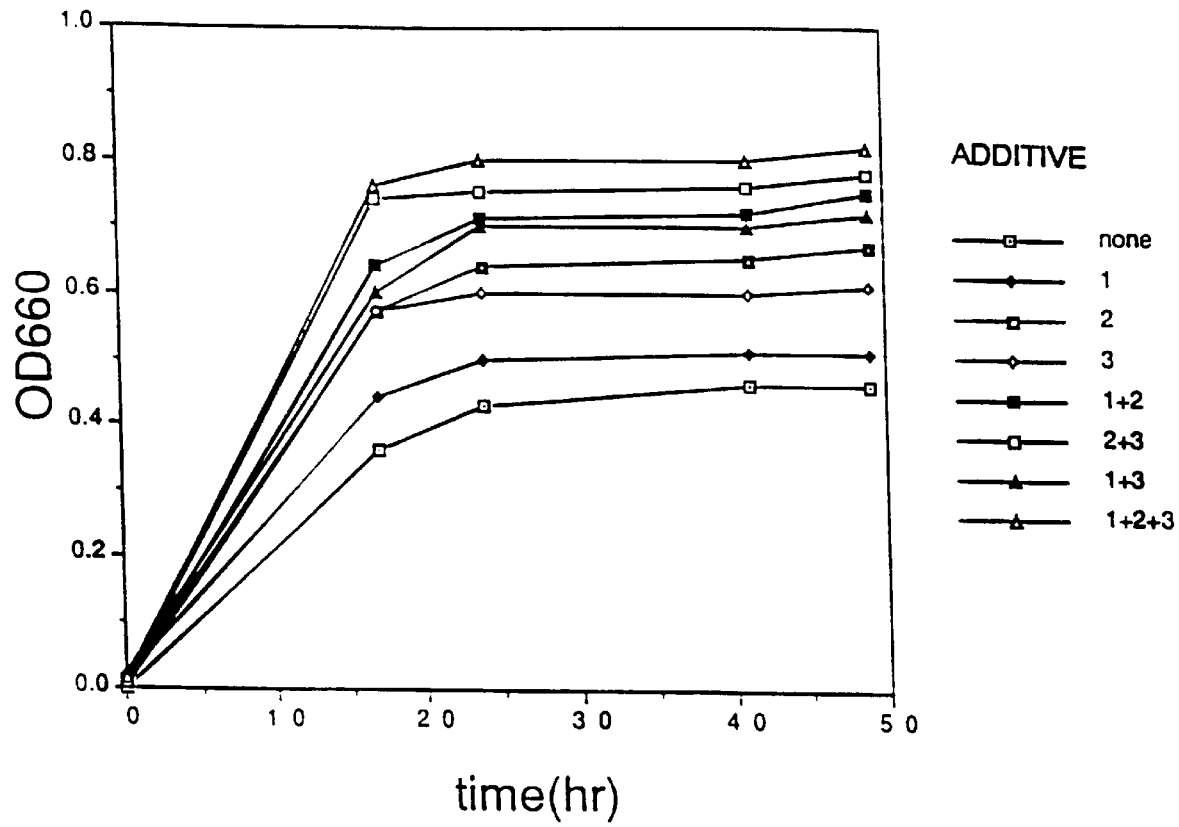
FIG. 7 shows influences exerted on growth by growth recovering factors.
Figure 8:
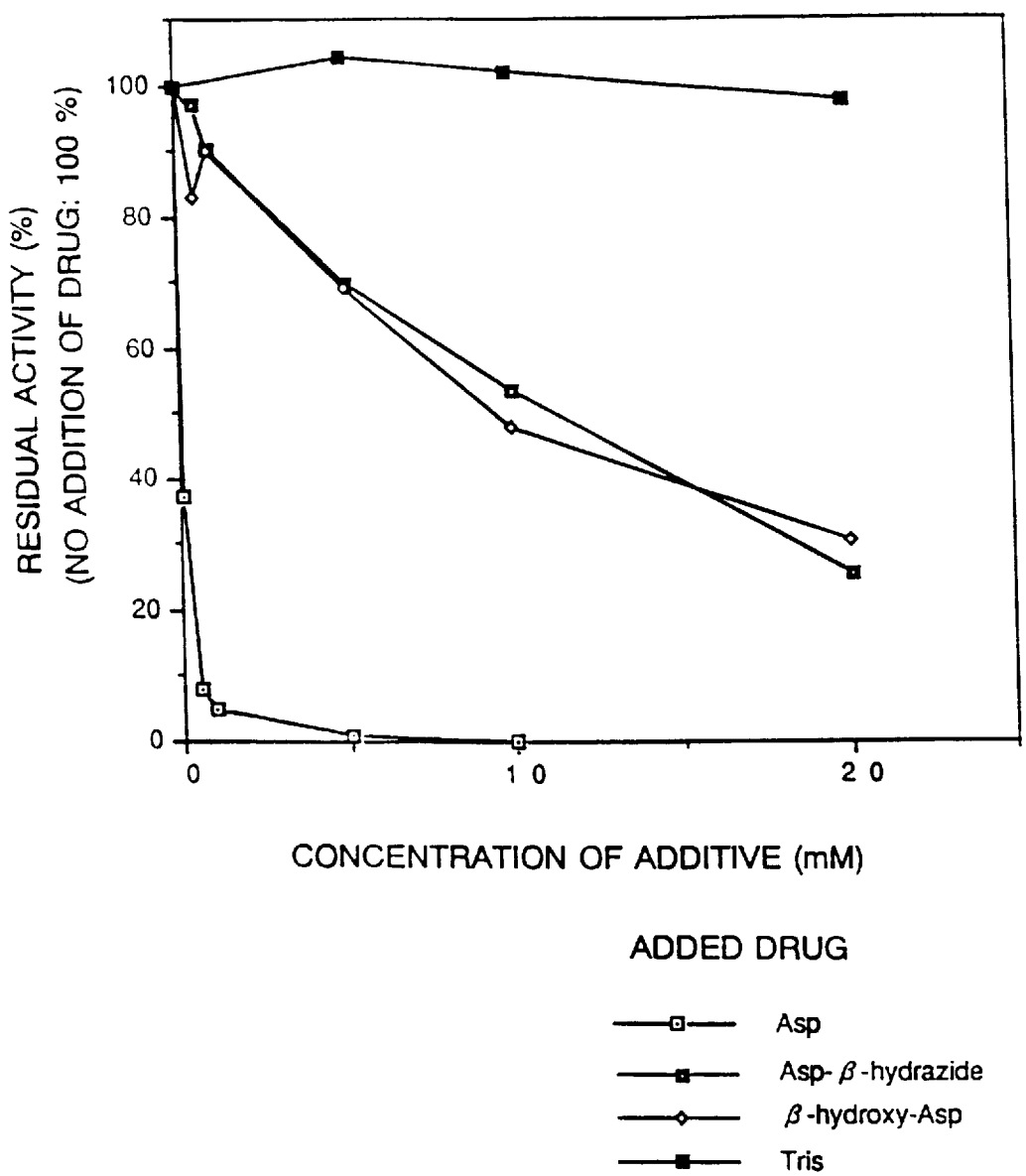
FIG. 8 shows inhibition of phosphoenolpyruvate carboxylase by growth inhibitory substances.

The present invention will be explained more concretely below with reference to Examples.

EXAMPLE 1

Acquisition of Mutant Phosphoenolpyruvate Carboxylase Gene

A mutant gene was prepared by using a plasmid pS2 obtained by inserting a phosphoenolpyruvate carboxylase gene having been cloned and determined for its base sequence into a SalI site of a vector plasmid pBR322. pS2 has an ampicillin resistance gene as a drug resistance marker gene (Sabe, H. et al., Gene, 31, 279–283 (1984)). The nucleotide sequence of the phosphoenolpyruvate carboxylase gene contained in pS2 is the same as that contained in the aforementioned plasmid pT2.

pS2 DNA was treated at 75° C. for 2 hours with a hydroxylamine treating solution (20 µg/ml pS2 DNA, 0.05M sodium phosphate (pH 6.0), 1 mM EDTA, 0.4M hydroxylamine). Because of influence by pH on the hydroxylamine treatment, 80 µl of 1M hydroxylamine.HCl and 1 mM EDTA solution having a pH adjusted to 6.0 with sodium hydroxide, 100 µl of 0.1M sodium phosphate (pH 6.0) and 1 mM EDTA solution, and TE (10 mM Tris-HCl, 1 mM EDTA) buffer containing 2 µg of pS2 DNA were mixed, to finally provide 200 µl with water.

The aforementioned condition is a condition in which transformants has a survival ratio of 0.2% based on a state before the treatment in an ampicillin-containing medium when *Escherichia coli* HB101 is transformed with pS2 after the treatment.

*Escherichia coli* HB101 was transformed with pS2 treated with hydroxylamine, which was spread on a solid plate medium containing ampicillin to obtain about 10000 colonies of transformants. They were suspended in a liquid medium, and spread on a solid plate medium containing any one of 3-bromopyruvate (3BP), aspartate-β-hydroxamate (AHX), aspartate-β-hydrazide (AHY) and DL-threo-β-hydroxyaspartate (βHA) as the analog compounds of aspartic acid at a concentration near a minimal inhibitory concentration to give $10^3$ to $10^5$ cells per one medium plate, and growing colonies were selected.

From 100 strains of analog compound resistant strains thus obtained, phosphoenolpyruvate carboxylase produced by each of them was partially purified in accordance with a method described in *The Journal of Biochemistry*, Vol. 67, No. 4 (1970), and inhibition of enzyme activity by the analog compounds was investigated. Measurement of the enzyme activity was performed in the same manner as described above.

Further, plasmids were isolated from bacterial strains producing mutant enzymes with activities not inhibited by the analog compounds, and were introduced into *Escherichia coli* PCR1 as a phosphoenolpyruvate carboxylase deficient strain (Sabe, H. et al., Gene, 31, 279–283 (1984)), to confirm production of the mutant enzymes.

Five transformants harboring mutant enzyme genes were thus obtained. As a result of determination of base sequences of these genes, 2 strains had the same mutation, and 4 kinds of mutant genes were obtained. The transformants harboring them were designated as AJ12907, AJ12908, AJ12909 and AJ12910, and were deposited in National Institute of Bioscience and Human Technology of Agency of Industrial Science and Technology 1-3, Higashi 1-chome, Tsukuba-shi, Ibaraki-ken, Japan; zip code 305) on Aug. 3, 1993 under the deposition numbers of FERM P-13774, FERM P-13775, FERM P-13776 and FERM P-13777, transferred from the original deposition to international deposition based on Budapest Treaty on Jul. 11, 1994 and has been deposited as deposition numbers of FERM BP-4734, FERM BP-4735, FERM BP-4736, FERM BP-4737, respectively in this order. Further, the plasmids possessed by them were designated as pBP5, pHA19, pBP122 and pR6 respectively in this order. Mutations possessed by the phosphoenolpyruvate carboxylase genes contained in each of the plasmids are shown in Table 2. Numerical values in the table indicate nucleotide numbers or amino acid numbers in SEQ ID NO:1.

TABLE 2

| Transformant | Plasmid | Mutation | Amino acid replacement associated with mutation |
|---|---|---|---|
| AJ12907 | pBP5 | $^{2109}G \to A$ | $^{625}Glu \to Lys$ |
| AJ12908 | PHA19 | $^{901}G \to A$ | $^{222}Arg \to His$ |
| | | $^{903}G \to A$ | $^{223}Glu \to Lys$ |
| AJ12909 | pBP122 | $^{1099}C \to T$ | $^{288}Ser \to Phe$ |
| | | $^{1101}G \to A$ | $^{289}Glu \to Lys$ |
| | | $^{1889}G \to A$ | $^{551}Met \to Ile$ |
| | | $^{2646}G \to A$ | $^{804}Glu \to Lys$ |
| AJ12910 | pR6 | $^{2835}G \to A$ | $^{867}Ala \to Thr$ |

Incidentally, selection was performed for AJ12907 and AJ12909 in a medium containing 500 μg/ml of 3BP, for AJ12908 in a medium containing 1000 μg/ml of βHA, and for AJ12910 in a medium containing 500 μg/ml of AHY.

EXAMPLE 2

Mutant Phosphoenolpyruvate Carboxylase

Sensitivity to aspartic acid was investigated for phosphoenolpyruvate carboxylases produced by the aforementioned 4 transformants. These bacterial strains are deficient in the phosphoenolpyruvate carboxylase gene originating from the host, so that produced phosphoenolpyruvate carboxylase originates from the plasmid.

Figure 9:
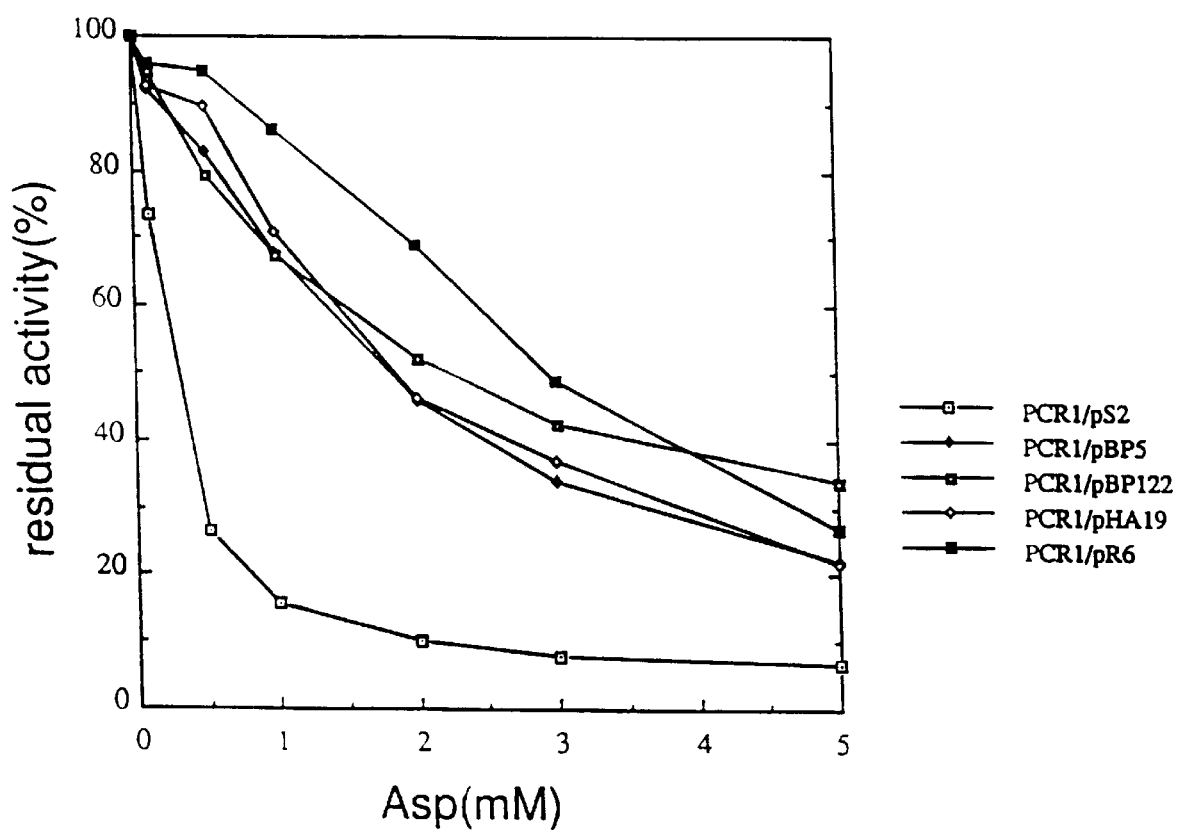
FIG. 9 shows inhibition of phosphoenolpyruvate carboxylase of the present invention by aspartic acid.
Figure 10:
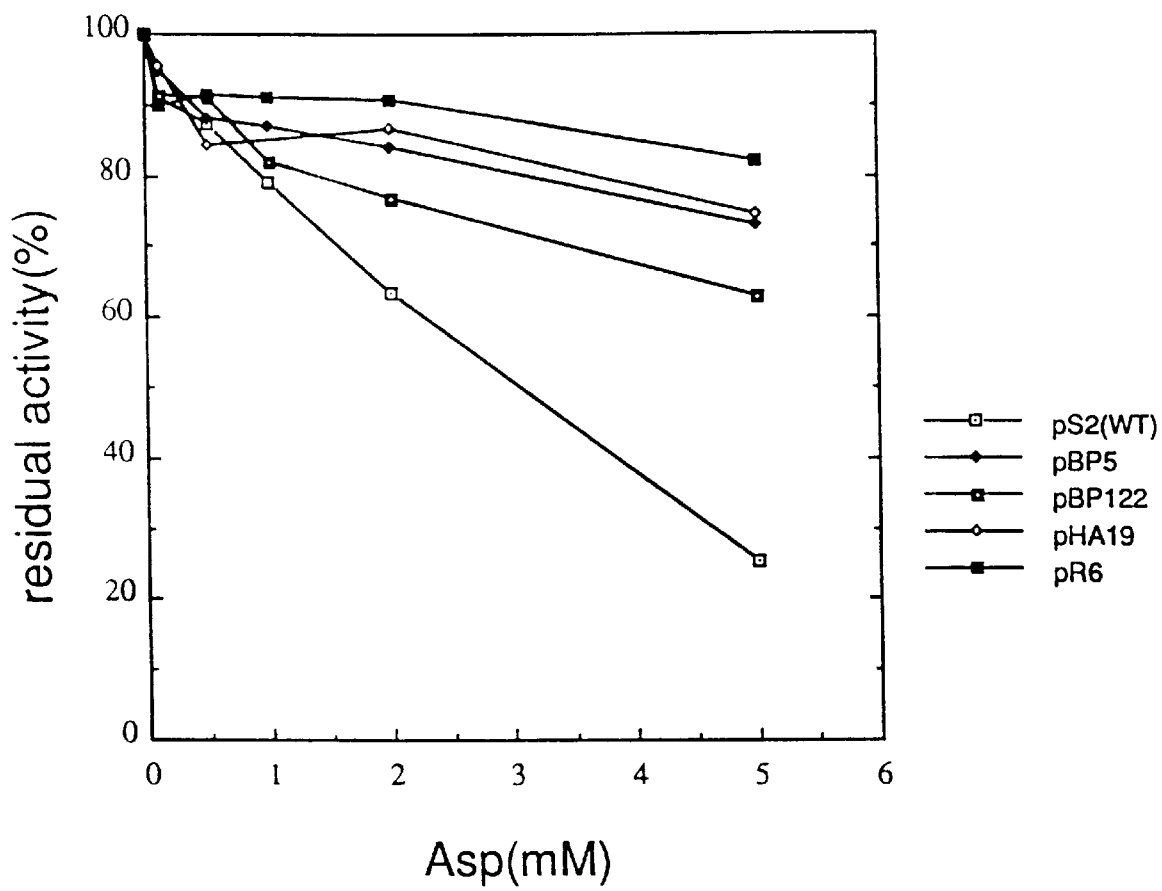
FIG. 10 shows inhibition of phosphoenolpyruvate carboxylase of the present invention by aspartic acid.

Sensitivity to aspartic acid was investigated in accordance with a known method (Yoshinaga, T., Izui, K. and Katsuki, H., *J. Biochem.*, 68, 747–750 (1970)). Namely, as a result of measurement of the enzyme activity produced by each of the transformants or *Escherichia coli* harboring pS2 in the presence of acetyl-coenzyme A known to affect the activity in an activity measurement system at a concentration of 0.1 mM or 1 mM, sensitivity to aspartic acid was measured as shown in FIGS. 9 and 10.

According to the result, it is apparent that the wild type enzyme loses its activity when aspartic acid is at a high concentration, while the mutant phosphoenolpyruvate carboxylase of the present invention substantially continues to maintain its activity.

EXAMPLE 3

Fermentative Production of L-threonine by *Escherichia coli* with Introduced Mutant Phosphoenolpyruvate Carboxylase As threonine-producing bacteria of *Escherichia coli*, B-3996 strain (Japanese Patent Laid-open No. 3-501682 (PCT)) has the highest production ability among those known at present. Thus upon evaluation of the mutant phosphoenolpyruvate carboxylase, B-3996 was used as the host. This B-3996 strain has been deposited in Research Institute for Genetics and Industrial Microorganism Breeding under a registration number of RIA 1867. Further, pBP5 was selected as the mutant phosphoenolpyruvate carboxylase to be evaluated, which was subjected to an experiment.

The plasmid pBP5 having the mutant phosphoenolpyruvate carboxylase was introduced into *Escherichia coli* B-3996 in accordance with a method of Hanahan (*J. Mol. Biol.*, Vol. 106, p577 (1983)), and a transformant was isolated. As a control, *Escherichia coli* B-3996 was transformed in the same manner with pS2 as the plasmid to express the wild type phosphoenolpyruvate carboxylase gene.

When *Escherichia coli* B-3996 and the transformants therefrom were respectively inoculated in a 500 ml of Sakaguchi flask poured with 20 ml of a medium having a composition in Table 3, and cultivated at 37° C. for 40 hours to investigate a production amount of L-threonine, then results shown in Table 4 were obtained. Incidentally, the aforementioned medium was separated into two: glucose and $MgSO_4 \cdot 7H_2O$, and the other components, and adjusted to have a pH of 7.0 with KOH followed by autoclaving at 115° C. for 10 minutes, and then, after mixing them, separately sterilized $CaCO_3$ was added by 30 g/l.

TABLE 3

| Component | Blending amount (g/l) |
|---|---|
| glucose | 40 |
| $(NH_4)_2SO_4$ | 16 |
| $KH_2PO_4$ | 1 |
| $MgSO_4 \cdot 7H_2O$ | 1 |
| $FeSO_4 \cdot 7H_2O$ | 0.01 |
| $MnSO_4 \cdot 5H_2O$ | 0.01 |
| yeast extract (Difco) | 2 |
| L-Met | 0.5 |
| $CaCO_3$ | 30 |

TABLE 4

| Bacterial strain | Threonine production amount (g/l) |
|---|---|
| *Escherichia coli* B-3996 | 15.7 |
| *Escherichia coli* B-3996/pS2 | 15.8 |
| *Escherichia coli* B-3996/pBP5 | 16.8 |

As clarified from the result, *Escherichia coli* B-3996/pBP5 harboring the mutant enzyme expression plasmid having the DNA sequence of the present invention had an improved threonine-producing ability as compared with *Escherichia coli* B-3996/pS2 harboring the plasmid to express the wild type enzyme.

EXAMPLE 4

Fermentative Production of L-glutamic Acid by *Escherichia coli* with Introduced Mutant Phosphoenolpyruvate Carboxylase As glutamic acid-producing bacteria of *Escherichia coli*, *Escherichia coli* AJ-12628 described in Japanese Patent Laid-open No. 4-11461 has the highest production ability among those known at present. Thus upon evaluation of the mutant phosphoenolpyruvate carboxylase, AJ-12628 was used as the host.

The AJ-12628 strain has been deposited in National Institute of Bioscience and Human Technology of Agency of Industrial Science and Technology under a registration number of FERM BP-385 Further, pBP5 was selected as the mutant phosphoenolpyruvate carboxylase to be evaluated, which was subjected to an experiment.

The plasmid pBP5 having the mutant phosphoenolpyruvate carboxylase was introduced into *Escherichia coli* AJ-12628 in accordance with a method of Hanahan (*J. Mol. Biol.*, Vol. 106, p577 (1983)), and a transformant was isolated. In the same manner, a transformant of *Escherichia coli* AJ-12628 with pS2 was isolated.

When *Escherichia coli* AJ-12628 and the transformants therefrom were respectively inoculated in a 500 ml of Sakaguchi flask poured with 20 ml of a medium having a composition in Table 5, and cultivated at 37° C. for 36 hours to investigate a production amount of L-glutamic acid, then results shown in Table 6 were obtained. Incidentally, the aforementioned medium was separated into two: glucose and $MgSO_4 \cdot 7H_2O$, and the other components, and adjusted to have a pH of 7.0 with KOH followed by autoclaving at 115° C. for 10 minutes, and then, after mixing them, separately sterilized $CaCO_3$ was added by 30 g/l.

TABLE 5

| Component | Blending amount (g/l) |
|---|---|
| glucose | 40 |
| $(NH_4)_2SO_4$ | 16 |
| $KH_2PO_4$ | 1 |
| $MgSO_4 \cdot 7H_2O$ | 1 |
| $FeSO_4 \cdot 7H_2O$ | 0.01 |
| $MnSO_4 \cdot 5H_2O$ | 0.01 |
| yeast extract (Difco) | 2 |
| $CaCO_3$ | 30 |

TABLE 6

| Bacterial strain | Glutamic acid production amount (g/l) |
|---|---|
| Escherichia coli AJ-12628 | 18.0 |
| Escherichia coli AJ-12628/pS2 | 18.3 |
| Escherichia coli AJ-12628/pBP5 | 19.6 |

As clarified from the result, *Escherichia coli* AJ-12628/pBP5 harboring the mutant enzyme expression plasmid having the DNA sequence of the present invention had an improved glutamate-producing ability as compared with *Escherichia coli* AJ-12628/pS2 harboring the plasmid to express the wild type enzyme.

EXAMPLE 5

Production of L-lysine by Coryneform Bacterium with Introduced Mutant Phosphoenolpyruvate Carboxylase In order to introduce and express the mutant gene in a coryneform bacterium, a promoter originating from a bacterium belonging to the genus Brevibacterium was obtained, and was ligated with the mutant gene to prepare an expression type plasmid. Further, it was introduced into a bacterium belonging to the genus Brevibacterium to perform production of L-lysine.

<1> Acquisition of aspartokinase (AK) gene originating from bacterium belonging to the genus Brevibacterium Chromosomal DNA was prepared according to an ordinary method from a *Brevibacterium lactofermentum* (*Corynebacterium glutamicum*) wild strain (ATCC 13869). An AK gene was amplified from the chromosomal DNA by PCR (polymerase chain reaction; see White, T. J. et al., *Trends Genet.*, 5, 185 (1989)). For DNA primers used in the amplification, an oligonucleotide of 23 mer (SEQ ID NO:3) and an oligonucleotide of 21 mer (SEQ ID NO:4) were synthesized to amplify a region of about 1643 bp coding for the AK gene based on a sequence known in *Corynebacterium glutamicum* (see *Molecular Microbiology* (1991) 5 (5), 1197–1204, *Mol. Gen. Genet.* (1990) 224, 317–324).

The synthesis of DNA was performed in accordance with an ordinary phosphoamidite method (see *Tetrahedron Letters* (1981), 22, 1859) using a DNA synthesizer model 380B produced by Applied Biosystems Co. In the PCR reaction, DNA Thermal Cycler PJ2000 type produced by Takara Shuzo Co., Ltd. was used, and gene amplification was performed by using Taq DNA polymerase in accordance with a method designated by the manufacturer.

An amplified gene fragment of 1643 kb was confirmed by agarose gel electrophoresis, and then the fragment cut out from the gel was purified by an ordinary method, and was cleaved with restriction enzymes NruI (produced by Takara Shuzo Co., Ltd.) and EcoRI (produced by Takara Shuzo Co., Ltd.). pHSG399 (see Takeshita, S. et al.; *Gene* (1987), 61, 63–74) was used for a cloning vector for the gene fragment. pHSG399 was cleaved with a restriction enzyme SmaI (produced by Takara Shuzo Co., Ltd.) and a restriction enzyme EcoRI, and ligated with the amplified AK gene fragment.

Ligation of DNA was performed by a designated method by using a DNA ligation kit (produced by Takara Shuzo Co., Ltd.). In such a manner, a plasmid was manufactured in which pHSG399 was ligated with the AK gene fragment amplified from Brevibacterium chromosome. The plasmid having the AK gene originating from ATCC 13869 as the wild strain was designated as p399AKY.

<2> Determination of base sequence of AK gene of *Brevibacterium lactofermentum*

The AK plasmid, p399AKY was prepared, and the base sequence of the AK gene was determined. Determination of the base sequence was performed in accordance with the method of Sanger et al. (F. Sanger et al.: *Proc. Natl. Acad. Sci. USA*, 74, 5463 (1977) and so forth). Results are shown in SEQ ID NO:5 and SEQ ID NO:7. The DNA fragments have two open reading frames which correspond to α-subunit and β-subunit of AK, respectively. In SEQ ID NO:5 and SEQ ID NO:7, amino acid sequences corresponding to each of the open reading frames are shown together with nucleotide sequences. Further, only the amino acid sequences corresponding to each of the open reading frames are shown in SEQ ID NO:6 and SEQ ID NO:8.

<3> Preparation of phosphoenolpyruvate carboxylase expression plasmid

SalI fragments of about 4.4 kb containing phosphoenolpyruvate carboxylase genes were extracted from pS2 as the plasmid having the wild type phosphoenolpyruvate carboxylase gene and pBP5 as the plasmid having the obtained mutant phosphoenolpyruvate carboxylase gene, and inserted into a SalI site of a plasmid vector pHSG399 universally used for *Escherichia coli*. Manufactured plasmids were designated as pHS2 for the wild type and as pHBP5 for the mutant.

In order to convert pHS2 and pHPB5 into plasmids to express in Brevibacterium, a promoter and a replication origin of a plasmid for functioning in Brevibacterium were introduced. As the promoter, a gene fragment containing one from 1st NruI site to 207th ApaLI site of the base sequence, which was postulated to be a promoter region of the cloned AK gene, was extracted from p399AKY, and inserted into an AvaI site located about 60 bp before the structural genes of pHS2 and pHBP5 to allow the transcription direction to be in a regular direction.

Further, a gene fragment to enable autonomously replication of the plasmid in Brevibacterium, namely the replication origin of the plasmid was introduced into a site located on the vector. A gene fragment containing the replication origin of the plasmid was extracted from a vector pHC4 for Brevibacterium (see paragraph No. 10 in Japanese Patent Laid-open No. 5-7491; *Escherichia coli* AJ12039 harboring the same plasmid is deposited in National Institute of Bioscience and Human Technology of Agency of Industrial Science and Technology, to which a deposition number of FERM P12215 is given), and restriction enzyme sites at both termini were modified into PstI sites by introduction of linkers.

This fragment was introduced into a PstI site in a vector portion of the plasmid added with the promoter derived from Brevibacterium. Constructed phosphoenolpyruvate carboxylase-expressing plasmids were designated as pHS2B for a wild type phosphoenolpyruvate carboxylase plasmid originating from pS2 and as pHBP5B for a mutant phosphoenolpyruvate carboxylase plasmid originating from pBP5, respectively.

<4> Production of L-lysine by using phosphoenolpyruvate carboxylase expression type plasmid Prepared pHS2B and pHBP5B were respectively introduced into AJ3463 as an L-lysine-producing bacterium of *Brevibacterium lactofermentum* (see Japanese Patent Publication No. 51-34477). For introduction of the gene, a transformation method employing electric pulse was used (see Japanese Patent Laid-open No. 2-207791). The host strain and transformants were cultivated with shaking for 72 hours at 31.5° C. in a lysine production medium having a composition in Table 7. The aforementioned medium was prepared such that those except for $CaCO_3$ among the components listed in the table were added to 1 l of water, and adjusted to have a pH of 8.0 with KOH followed by autoclaving at 115° C. for 15 minutes, and then $CaCO_3$ having been subjected to heat sterilization was further added. Accumulated amounts of L-lysine in the medium after cultivation are shown in Table 8.

TABLE 7

| Component | Blending amount in 1 L |
| --- | --- |
| glucose | 100 g |
| $(NH_4)_2SO_4$ | 55 g |
| soybean concentrate* | 35 m/l |
| $KH_2PO_4$ | 1 g |
| $MgSO_4.7H_2O$ | 1 g |
| Vitamin B1 | 20 g |
| biotin | 5 g |
| nicotinic acid amide | 5 mg |
| $FeSO_4.7H_2O$ | 0.01 g |
| $MnSO_4.5H_2O$ | 0.01 g |
| $CaCO_3$ | 50 g |

*product of Ajinomoto Co., Ltd. (trade name: Mamenou)

TABLE 8

| Bacterial strain | Lysine production amount (g/l) |
| --- | --- |
| *Brevibacterium lactofermentum* AJ3463 | 20.0 |
| *Brevibacterium lactofermentum* AJ3463/pHS2B | 22.0 |
| *Brevibacterium lactofermentum* AJ3463/pHBP5B | 25.0 |

As shown in the result, *Brevibacterium lactofermentum* AJ3463/pHBP5B harboring the mutant enzyme expression plasmid having the DNA sequence of the present invention had an improved lysine-producing ability as compared with *Brevibacterium lactofermentum* AJ3463/pHS2B harboring the plasmid to express the wild type enzyme.

EXAMPLE 6

Another Example of Mutant Phosphoenolpyruvate Carboxylase of the Present Invention and its Gene <1> Preparation of mutant phosphoenolpyruvate carboxylase gene Upon preparation of DNA coding for a mutant phosphoenolpyruvate carboxylase, a phosphoenolpyruvate carboxylase gene cloned in a plasmid pT2 was used as a material.

A host, which is allowed to harbor the plasmid pT2, is preferably deficient in phosphoenolpyruvate carboxylase gene in order to detect only the activity of phosphoenolpyruvate carboxylase originating from the plasmid. *Escherichia coli* F15 (Hfr, recA1, met, Δ(ppc-argECBH), Tn10) was used as such a deficient strain. *Escherichia coli* AJ-12873, which is allowed to harbor pT2 in F15 strain, is deposited as FERM P-13752 in National Institute of Bioscience and Human Technology of Agency of Industrial Science and Technology (1-3, Higashi 1-chome, Tsukuba-shi, Ibaraki-ken, Japan; zip code 305) on Jul. 15, 1993, transferred from the original deposition to international deposition based on Budapest Treaty on Jul. 11, 1994 and has been deposited as deposition number of FERM BP-4732. In addition, an entire base sequence of pT2 is shown in SEQUENCE ID NO:1.

In order to replace a codon of 438th arginine of the phosphoenolpyruvate carboxylase into a codon of cysteine by using pT2, the Overlapping Extension method (Ho, S. N., Hunt, H. D., Horton, R. M., Pullen, J. K. and Pease, L. R., Gene, 77, 51–59 (1989)) utilizing the PCR (Polymerase Chain Reaction) method was used.

Incidentally, the PCR method is a method in which an amplification cycle comprising thermal denaturation of double strand DNA into single strand DNA, annealing of oligonucleotide primers corresponding to sequences at both ends of a site aimed to be amplified and the aforementioned thermally denatured DNA, and polymerase reaction using the aforementioned oligonucleotides as primers is repeated, thereby the aforementioned DNA sequence is amplified in a manner of an exponential function.

Figure 11:
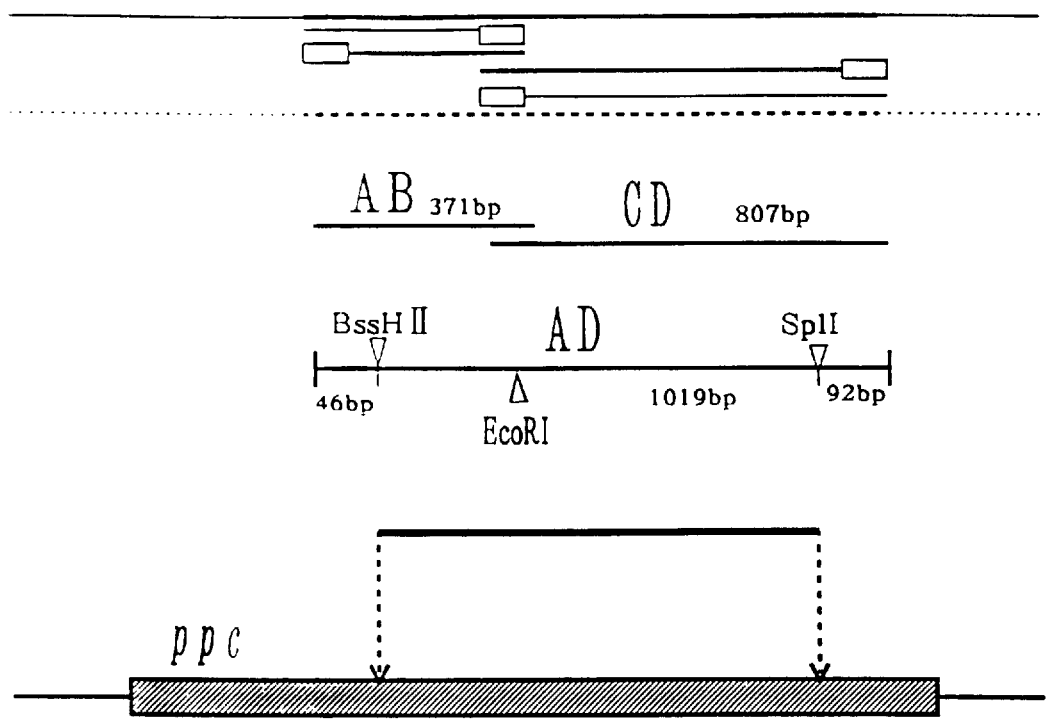
FIG. 11 shows a method for introducing mutation into a phosphoenolpyruvate carboxylase gene.

A region subjected to site specific mutation by the PCR method is shown in FIG. 11. The primers used in the present invention were 4 species of a primer c (SEQUENCE ID NO:11, corresponding to base Nos. 1535–1554 in SEQUENCE ID NO:1) having a sequence in the vicinity of the codon of 438th arginine, a primer b (SEQUENCE ID NO:10) having a sequence complement to the primer c, a primer a (SEQUENCE ID NO:9, corresponding to base Nos. 1185–1200 in SEQUENCE ID NO:1) having a sequence upstream therefrom, and a primer d (SEQUENCE ID NO:12, corresponding to base Nos. 2327–2342 in SEQUENCE ID NO:1) having a sequence complement to a downstream sequence.

In the primer b and the primer c, the codon (CGT) of 438th arginine was replaced with a codon (TGT) of cysteine. This replacement may use TGC which is another codon of cysteine. Further, C of the third letter of a codon (AAC) of 435th asparagine was replaced with T, and hence an EcoRI site was internally introduced with no replacement of amino acid, so that a mutant plasmid could be selected by using it as an index. However, this mutation is not essential to the present invention.

When the PCR reaction was performed by using pT2 DNA as a template and the primer a and the primer b as the primers, a fragment from the upstream of the mutation site to the mutation site (AB fragment in FIG. 11) was amplified. Further, when the PCR reaction was performed by using the primer c and the primer d, a fragment downstream from the mutation site (CD fragment in FIG. 11) was amplified. When each of the amplified products (AB, CD) was annealed again after thermal denaturation to perform a polymerase reaction, they were ligated to obtain a fragment (AD fragment in FIG. 11). Incidentally, the PCR reaction was performed by repeating 30 cycles of each comprising heating at 94° C. for 1 minute followed by denaturation (94° C., 1.5 minutes), annealing (50° C., 2 minutes), and elongation reaction by polymerase (72° C., 3.5 minutes). In addition, reaction compositions are shown in Table 9.

TABLE 9

| Composition (( ): final conc.) | PCR fragment | | |
|---|---|---|---|
| | AB | CD | AD |
| H₂O | 53.5 | 53.5 | 53.5 |
| 10-fold reaction buffer | 10 | 10 | 10 |
| mixture of 1.25 mM dNTP | 16 | 16 | 16 |
| 20 μM primer a (1 μM) | 5 | — | 5 |
| 20 μM primer b (1 μM) | 5 | — | — |
| 20 μM primer c (1 μM) | — | 5 | — |
| 20 μM primer d (1 μM) | — | 5 | 5 |
| 10 μg/μl pT2 (0.1 μg) | 10 | 10 | — |
| PCR fragment AB* | — | — | 5 |
| PCR fragment CD* | — | — | 5 |
| 2.5 U/μl Tag polymerase | 0.5 | 0.5 | 0.5 |
| total amount | 100 μl | 100 μl | 100 μl |

*PCR fragments AB and CD were prepared, after the PCR reaction, by recovering 10 μl thereof from polyacrylamide gel, and dissolving it in 5 μl of TE (10 mM Tris-HCl (pH 8.0), 1 mM EDTA (pH 8.0)).

In the AD fragment obtained as described above, a BssHII site (1231–1236 in SEQ ID NO:1) at the upstream side and a SplI site (2249–2254 in SEQ ID NO:1) at the downstream side were present, so that complete digestion was performed with these enzymes to make replacement for a corresponding region of the plasmid pT2 (FIG. 11).

<2> Selection of inhibition-desensitized phosphoenolpyruvate carboxylase

Escherichia coli was transformed with a plasmid obtained as described above, and a transformed strain was cultivated to recover the plasmid to select one cleaved by EcoRI. With respect to selected DNA, a base sequence of the region amplified by the aforementioned PCR method was determined by the dideoxy method to confirm that base replacement as exactly aimed was introduced. This plasmid was designated as pT2R438C. A strain (AJ12874) obtained by introducing this plasmid into the aforementioned Escherichia coli F15 has been deposited as FERM P-13753 in National Institute of Bioscience and Human Technology of Agency of Industrial Science and Technology (1-3, Higashi 1-chome, Tsukuba-shi, Ibaraki-ken, Japan; zip code 305) on Jul. 15, 1993, transferred from the original deposition to international deposition based on Budapest Treaty on Jul. 11, 1994 and has been deposited as deposition number of FERM BP-4733.

The base sequence of pT2R438C is a sequence in which 1541th and 1550th nucleotides are replaced from C to T respectively in SEQ ID NO:1.

<3> Confirmation of desensitization of inhibition of mutant phosphoenolpyruvate carboxylase by aspartic acid Sensitivity to aspartic acid was investigated for phosphoenolpyruvate carboxylase produced by the aforementioned Escherichia coli AJ12874 harboring pT2R438C. Incidentally, as described above, because the Escherichia coli F15 is deficient in phosphoenolpyruvate carboxylase, phosphoenolpyruvate carboxylase produced by AJ12874 originates from the plasmid.

Figure 12A:
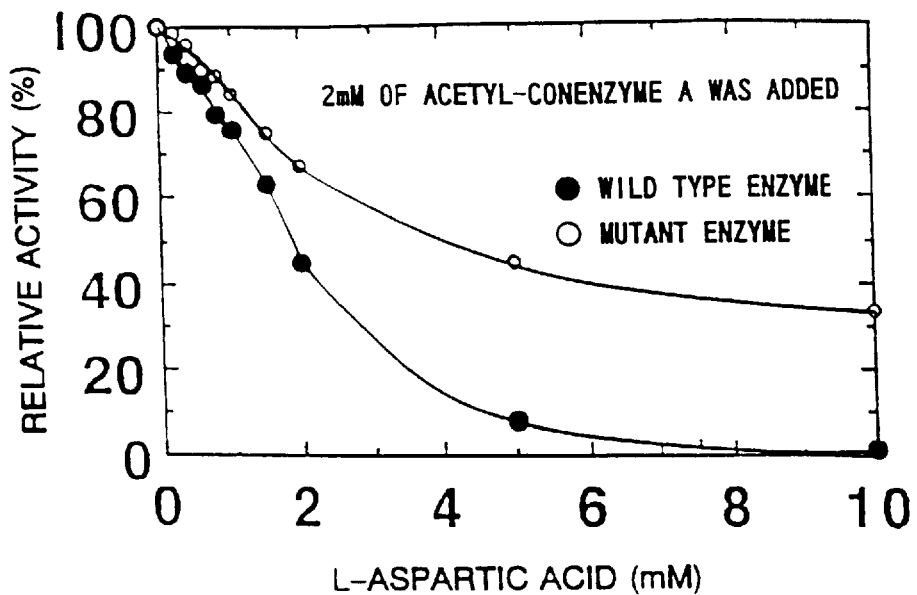
FIG. 12 shows influences exerted by aspartic acid on acitivities of wild type and mutant phosphoenolpyruvate carboxylase in which 438th arginine was substituted with cysteine counted from the N-terminus.
Figure 12B:
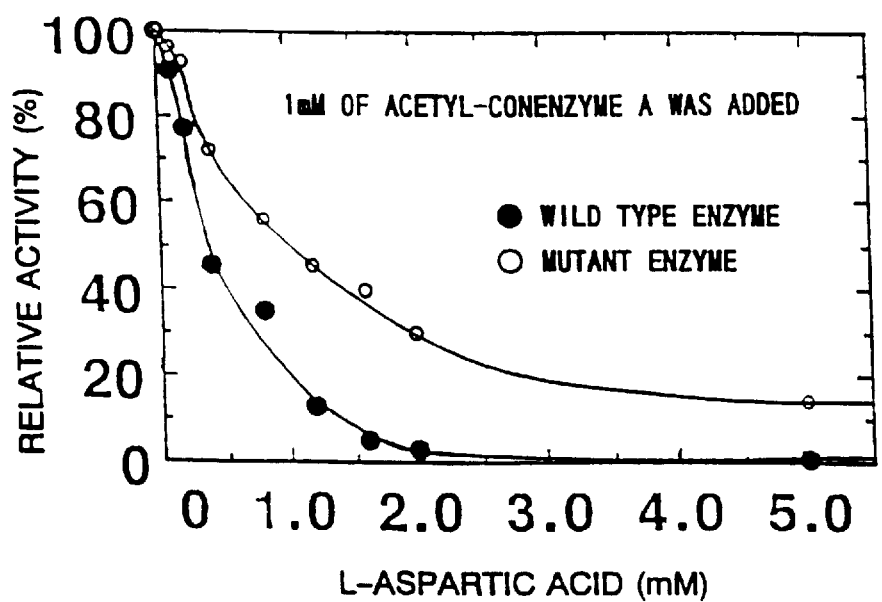

Sensitivity to aspartic acid was investigated in accordance with a known method (Yoshinaga, T., Izui, K. and Katsuki, H., J. Biochem., 68, 747–750 (1970)). Namely, as a result of measurement of the enzyme activity in the presence of acetyl-coenzyme A known to affect the activity in an activity measurement system at a concentration of 1 mM or 2 mM, sensitivity to aspartic acid was measured as shown in FIG. 12.

It is apparent that the wild type enzyme substantially loses its activity when aspartic acid is at a high concentration, while the mutant phosphoenolpyruvate carboxylase of the present invention continues to maintain its activity.

<4> Preparation of mutant phosphoenolpyruvate carboxylase gene (II)

In order to replace a codon of 620th lysine with a codon of serine in the phosphoenolpyruvate carboxylase gene carried on the plasmid pT2, the overlapping Extension method (Ho, S. N., Hunt, H. D., Horton, R. M., Pullen, J. K. and Pease, L. R., Gene, 77, 51–59 (1989)) utilizing the PCR (Polymerase Chain Reaction) method was used. Concrete procedures were in accordance with the method described in <1>. A plasmid carrying a mutant gene constructed with aimed replacement was designated as pT2K620S. Further, an obtained mutant enzyme was designated as K620S mutant enzyme.

<5> Confirmation of desensitization of inhibition by aspartic acid concerning mutant phosphoenolpyruvate carboxylase.

With respect to the phosphoenolpyruvic carboxylase produced by a transformant obtained by introducing the plasmid pT2K620S into the aforementioned Escherichia coli F15, sensitivity to aspartic acid was investigated. Incidentally, as described above, since the Escherichia coli F15 lacks phosphoenolpyruvate carboxylase, any phosphoenolpyruvate carboxylase produced by the transformant originates from the plasmid.

Sensitivity to aspartic acid was investigated in accordance with a known method (Yoshinaga, T., Izui, K. and Katsuki, H., J. Biochem., 68, 747–750 (1970)). Namely, as a result of measurement of the enzyme activity in the presence of acetyl-coenzyme A known to affect the activity in an activity measurement system at a concentration of 1 mM or 2 mM, sensitivity to aspartic acid was measured as shown in FIG. 13.

It is apparent that the wild enzyme substantially loses its activity when aspartic acid is at a high concentration, while the type phosphoenolpyruvate carboxylase of the present invention continues to maintain its activity.

Figure 13A:
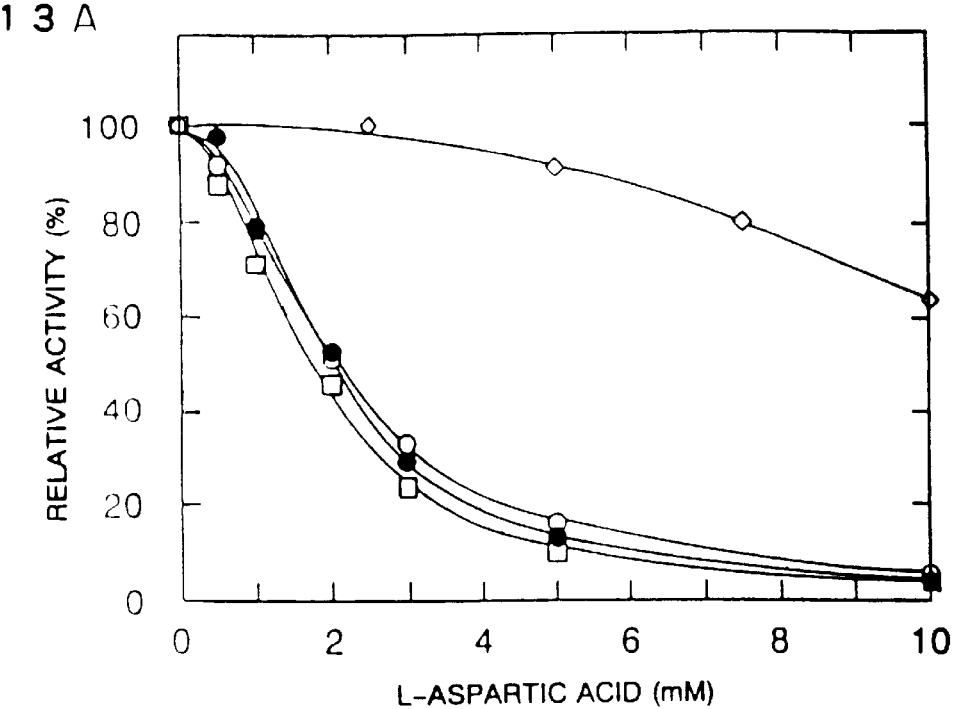
FIG. 13 shows the influence exerted by (a) 1–10 mM and (b) 1–50 mM of aspartic acid on the activities of the wild-type (solid circles) of E. coli phosphoenolpyruvate carboxylase and its mutants Lys-620Ser (diamonds), Lys-650Ala (open circles), and Lys-491Ala (squares).
Figure 13B:
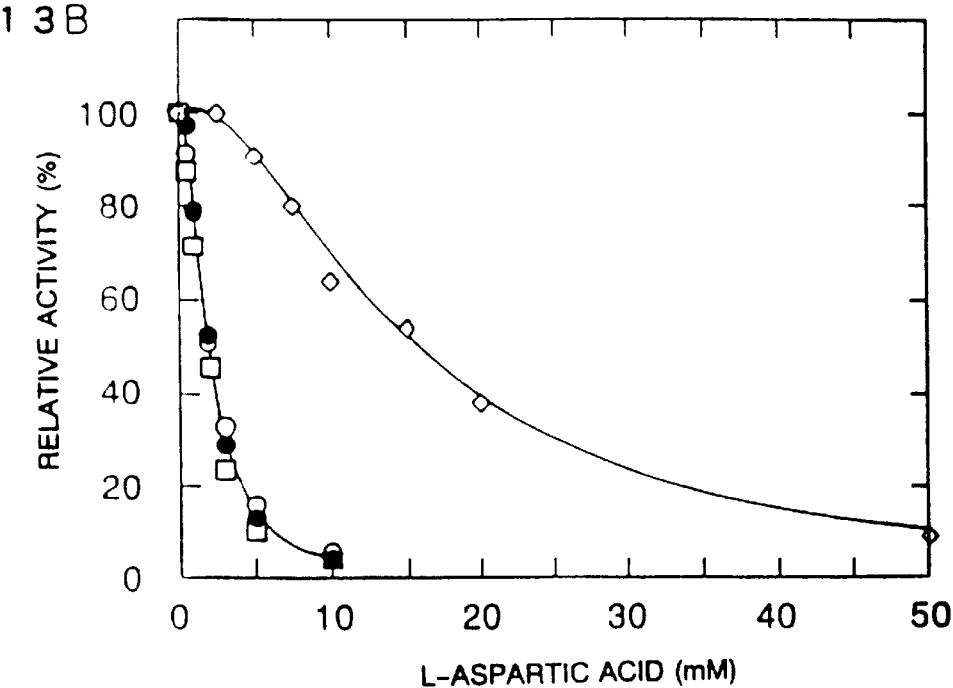

In FIG. 13, sensitivity to aspartic acid is also depicted for a mutant phosphoenolpyruvate carboxylase in which 650th lysine is replaced with alanime (K650A mutant enzyme), and for a mutant phosphoenolpyruvate carboxylase in which 491th lysine is replaced with serine (K491A mutant enzyme). In the case of these mutant enzymes, inhibition by aspartic acid was not desensitized.

INDUSTRIAL APPLICABILITY

The DNA sequence of the present invention codes for the mutant phosphoenolpyruvate carboxylase, and the microorganism harboring this DNA sequence produces the aforementioned enzyme.

The mutant phosphoenolpyruvate carboxylase of the present invention does not substantially undergo activity inhibition by aspartic acid, so that it can be utilized for fermentative production of amino acids subjected to regulation of biosynthesis by aspartic acid and the like.

What is claimed is:

1. A method of producing an amino acid, comprising:
selecting a microorganism of the genus Escherichia containing a DNA sequence encoding a mutant phosphoenolpyruvate carboxylase desensitized to feedback inhibition by aspartic acid by growing Escherichia microorganisms in the presence of a wild-type phosphoenolpyruvate carboxylase inhibitor selected from the group consisting of 3-bromopyruvate, aspartic acid-β-hydrazide and DL-threo-β-hydroxyaspartic acid;
culturing a microorganism of the genus Escherichia or coryneform bacteria transformed with the DNA sequence encoding a mutant phosphoenolpyruvate carboxylase in a suitable medium; and
separating from the medium an amino acid selected from the group consisting of L-lysine, L-threonine, L-methionine, L-isoleucine, L-glutamic acid, L-arginine and L-proline.

2. The method of claim 1, wherein the mutant phosphoenolpyruvate carboxylase has the glutamic acid residue at the $625^{th}$ position from the N-terminus mutated to an amino acid residue other than glutamic acid.

3. A method according to claim 1, wherein the mutant phosphoenolpyruvate carboxylase has the glutamic acid residue at the $625^{th}$ position from the N-terminus replaced with lysine.

4. A method according to claim 1, wherein the mutant phosphoenolpyruvate carboxylase has the arginine residue at the $222^{nd}$ position mutated to an amino acid residue other than arginine and the glutamic acid residue at the $223^{rd}$ position mutated to an amino acid residue other than glutamic acid, wherein the amino acid positions are measured from the N-terminus of the phosphoenolpyruvate carboxylase.

5. A method according to claim 1, wherein the mutant phosphoenolpyruvate carboxylase has the arginine residue at the $222^{nd}$ position replaced with histidine and the glutamic acid residue at the $223^{rd}$ position replaced with lysine, wherein the amino acid positions are measured from the N-terminus of the phosphoenolpyruvate carboxylase.

6. A method according to claim 1, wherein the mutant phosphoenolpyruvate carboxylase has the serine residue at the $288^{th}$ position mutated to an amino acid residue other than serine, the glutamic acid residue at the $289^{th}$ position mutated to an amino acid residue other than glutamic acid, the methionine residue at the $551^{st}$ position mutated to an amino acid other than methionine, and the glutamic acid residue at the $804^{th}$ position mutated to an amino acid other than glutamic acid, wherein the amino acid positions are measured from the N-terminus of the phosphoenolpyruvate carboxylase.

7. A method according to claim 1, wherein the mutant phosphoenolpyruvate carboxylase has the serine residue at the $288^{th}$ position replaced with phenylalanine, the glutamic acid residue at the $289^{th}$ position replaced with lysine, the methionine residue at the $551^{st}$ position replaced with isoleucine, and the glutamic acid residue at the 804$^{th}$ position replaced with lysine, wherein the amino acid positions are measured from the N-terminus of the phosphoenolpyruvate carboxylase.

8. A method according to claim 1, wherein the mutant phosphoenolpyruvate carboxylase has the alanine residue at the 867$^{th}$ position as measured from the N-terminus mutated to an amino acid residue other than alanine.

9. A method according to claim 1, wherein the mutant phosphoenolpyruvate carboxylase has the alanine residue at the 867$^{th}$ position as measured from the N-terminus replaced with threonine.

10. A method of producing amino acid, comprising:

cultivating a microorganism belonging to the genus Escherichia or coryneform bacteria in a suitable medium; and separating, from the medium, an amino acid selected from the group consisting of L-lysine, L-threonine, L-methionine, L-isoleucine, L-glutamic acid, L-arginine and L-proline, wherein the microorganism is transformed by allowing a DNA fragment to be integrated in chromosomal DNA or transformed with a recombinant DNA formed by ligating the DNA fragment with a vector DNA capable of autonomously replication in cells of bacteria belonging to the genus Escherichia or coryneform bacteria, wherein the DNA fragment encodes a mutant phosphoenolpyruvate carboxylase originating from a microorganism belonging to the genus Escherichia; the mutant phosphoenolpyruvate carboxylase has mutation to desensitize feedback inhibition of the phosphoenolpyruvate carboxylase by aspartic acid; and the mutant phosphoenolpyruvate carboxylase has the arginine residue at the 438$^{th}$ position from the N-terminus mutated to an amino acid residue other than arginine.

11. A method according to claim 10, wherein the mutant phosphoenolpyruvate carboxylase has the arginine residue at the 438$^{th}$ position replaced with cysteine.

12. A method of producing amino acid, comprising:

cultivating a microorganism belonging to the genus Escherichia or coryneform bacteria in a suitable medium; and separating, from the medium, an amino acid selected from the group consisting of L-lysine, L-threonine, L-methionine, L-isoleucine, L-glutamic acid, L-arginine and L-proline, wherein the microorganism is transformed by allowing a DNA fragment to be integrated in chromosomal DNA or transformed with a recombinant DNA formed by ligating the DNA fragment with a vector DNA capable of autonomously replication in cells of bacteria belonging to the genus Escherichia or coryneform bacteria; the DNA fragment encodes a mutant phosphoenolpyruvate carboxylase originating from a microorganism belonging to the genus Escherichia; the mutant phosphoenolpyruvate carboxylase has mutation to desensitize feedback inhibition of the phosphoenolpyruvate carboxylase by aspartic acid; and the mutant phosphoenolpyruvate carboxylase has the lysine residue at the 620$^{th}$ position from the N-terminus mutated to an amino acid residue other than lysine.

13. A method according to claim 12, wherein the mutant phosphoenolpyruvate carboxylase has the lysine residue at the 620$^{th}$ position replaced with serine.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 5186 base pairs
        ( B ) TYPE: nucleic acid
        ( C ) STRANDEDNESS: double
        ( D ) TOPOLOGY: circular ( i i ) MOLECULE TYPE: DNA (genomic)

( i v ) ANTI-SENSE: NO ( v i ) ORIGINAL SOURCE:
        ( A ) ORGANISM: Escherichia coli ( i x ) FEATURE:
        ( A ) NAME/KEY: CDS
        ( B ) LOCATION: 237..2888

( x i ) SEQUENCE DESCRIPTION: SEQ ID NO:1:

```
TCGACCGGCG ATTTTTTAAC ATTTCCATAA GTTACGCTTA TTTAAAGCGT CGTGAATTTA          60

ATGACGTAAA TTCCTGCTAT TTATTCGTTT GCTGAAGCGA TTTCGCAGCA TTTGACGTCA         120

CCGCTTTTAC GTGGCTTTAT AAAAGACGAC GAAAAGCAAA GCCCGAGCAT ATTCGCGCCA         180

ATGCGACGTG AAGGATACAG GGCTATCAAA CGATAAGATG GGGTGTCTGG GGTAAT            236

ATG AAC GAA CAA TAT TCC GCA TTG CGT AGT AAT GTC AGT ATG CTC GGC          284
Met Asn Glu Gln Tyr Ser Ala Leu Arg Ser Asn Val Ser Met Leu Gly
 1               5                  10                  15

AAA GTG CTG GGA GAA ACC ATC AAG GAT GCG TTG GGA GAA CAC ATT CTT          332
Lys Val Leu Gly Glu Thr Ile Lys Asp Ala Leu Gly Glu His Ile Leu
             20                  25                  30

GAA CGC GTA GAA ACT ATC CGT AAG TTG TCG AAA TCT TCA CGC GCT GGC          380
Glu Arg Val Glu Thr Ile Arg Lys Leu Ser Lys Ser Ser Arg Ala Gly
         35                  40                  45

AAT GAT GCT AAC CGC CAG GAG TTG CTC ACC ACC TTA CAA AAT TTG TCG          428
Asn Asp Ala Asn Arg Gln Glu Leu Leu Thr Thr Leu Gln Asn Leu Ser
     50                  55                  60

AAC GAC GAG CTG CTG CCC GTT GCG CGT GCG TTT AGT CAG TTC CTG AAC          476
Asn Asp Glu Leu Leu Pro Val Ala Arg Ala Phe Ser Gln Phe Leu Asn
 65                  70                  75                  80

CTG GCC AAC ACC GCC GAG CAA TAC CAC AGC ATT TCG CCG AAA GGC GAA          524
Leu Ala Asn Thr Ala Glu Gln Tyr His Ser Ile Ser Pro Lys Gly Glu
                 85                  90                  95

GCT GCC AGC AAC CCG GAA GTG ATC GCC CGC ACC CTG CGT AAA CTG AAA          572
Ala Ala Ser Asn Pro Glu Val Ile Ala Arg Thr Leu Arg Lys Leu Lys
            100                 105                 110

AAC CAG CCG GAA CTG AGC GAA GAC ACC ATC AAA AAA GCA GTG GAA TCG          620
Asn Gln Pro Glu Leu Ser Glu Asp Thr Ile Lys Lys Ala Val Glu Ser
        115                 120                 125

CTG TCG CTG GAA CTG GTC CTC ACG GCT CAC CCA ACC GAA ATT ACC CGT          668
Leu Ser Leu Glu Leu Val Leu Thr Ala His Pro Thr Glu Ile Thr Arg
    130                 135                 140

CGT ACA CTG ATC CAC AAA ATG GTG GAA GTG AAC GCC TGT TTA AAA CAG          716
Arg Thr Leu Ile His Lys Met Val Glu Val Asn Ala Cys Leu Lys Gln
145                 150                 155                 160

CTC GAT AAC AAA GAT ATC GCT GAC TAC GAA CAC AAC CAG CTG ATG CGT          764
Leu Asp Asn Lys Asp Ile Ala Asp Tyr Glu His Asn Gln Leu Met Arg
                165                 170                 175
```

| | | | | | | | | | | | | | | | | |
|---|---|---|---|---|---|---|---|---|---|---|---|---|---|---|---|---|
| CGC | CTG | CGC | CAG | TTG | ATC | GCC | CAG | TCA | TGG | CAT | ACC | GAT | GAA | ATC | CGT | 812 |
| Arg | Leu | Arg | Gln | Leu | Ile | Ala | Gln | Ser | Trp | His | Thr | Asp | Glu | Ile | Arg | |
| | | | 180 | | | | | 185 | | | | | 190 | | | |
| AAG | CTG | CGT | CCA | AGC | CCG | GTA | GAT | GAA | GCC | AAA | TGG | GGC | TTT | GCC | GTA | 860 |
| Lys | Leu | Arg | Pro | Ser | Pro | Val | Asp | Glu | Ala | Lys | Trp | Gly | Phe | Ala | Val | |
| | | 195 | | | | | 200 | | | | | 205 | | | | |
| GTG | GAA | AAC | AGC | CTG | TGG | CAA | GGC | GTA | CCA | AAT | TAC | CTG | CGC | GAA | CTG | 908 |
| Val | Glu | Asn | Ser | Leu | Trp | Gln | Gly | Val | Pro | Asn | Tyr | Leu | Arg | Glu | Leu | |
| | 210 | | | | | 215 | | | | | 220 | | | | | |
| AAC | GAA | CAA | CTG | GAA | GAG | AAC | CTC | GGC | TAC | AAA | CTG | CCC | GTC | GAA | TTT | 956 |
| Asn | Glu | Gln | Leu | Glu | Glu | Asn | Leu | Gly | Tyr | Lys | Leu | Pro | Val | Glu | Phe | |
| 225 | | | | | 230 | | | | | 235 | | | | | 240 | |
| GTT | CCG | GTC | CGT | TTT | ACT | TCG | TGG | ATG | GGC | GGC | GAC | CGC | GAC | GGC | AAC | 1004 |
| Val | Pro | Val | Arg | Phe | Thr | Ser | Trp | Met | Gly | Gly | Asp | Arg | Asp | Gly | Asn | |
| | | | | 245 | | | | | 250 | | | | | 255 | | |
| CCG | AAC | GTC | ACT | GCC | GAT | ATC | ACC | CGC | CAC | GTC | CTG | CTA | CTC | AGC | CGC | 1052 |
| Pro | Asn | Val | Thr | Ala | Asp | Ile | Thr | Arg | His | Val | Leu | Leu | Leu | Ser | Arg | |
| | | | 260 | | | | | 265 | | | | | 270 | | | |
| TGG | AAA | GCC | ACC | GAT | TTG | TTC | CTG | AAA | GAT | ATT | CAG | GTG | CTG | GTT | TCT | 1100 |
| Trp | Lys | Ala | Thr | Asp | Leu | Phe | Leu | Lys | Asp | Ile | Gln | Val | Leu | Val | Ser | |
| | | 275 | | | | | 280 | | | | | 285 | | | | |
| GAA | CTG | TCG | ATG | GTT | GAA | GCG | ACC | CCT | GAA | CTG | CTG | GCG | CTG | GTT | GGC | 1148 |
| Glu | Leu | Ser | Met | Val | Glu | Ala | Thr | Pro | Glu | Leu | Leu | Ala | Leu | Val | Gly | |
| | 290 | | | | | 295 | | | | | 300 | | | | | |
| GAA | GAA | GGT | GCC | GCA | GAA | CCG | TAT | CGC | TAT | CTG | ATG | AAA | AAC | CTG | CGT | 1196 |
| Glu | Glu | Gly | Ala | Ala | Glu | Pro | Tyr | Arg | Tyr | Leu | Met | Lys | Asn | Leu | Arg | |
| 305 | | | | | 310 | | | | | 315 | | | | | 320 | |
| TCT | CGC | CTG | ATG | GCG | ACA | CAG | GCA | TGG | CTG | GAA | GCG | CGC | CTG | AAA | GGC | 1244 |
| Ser | Arg | Leu | Met | Ala | Thr | Gln | Ala | Trp | Leu | Glu | Ala | Arg | Leu | Lys | Gly | |
| | | | | 325 | | | | | 330 | | | | | 335 | | |
| GAA | GAA | CTG | CCA | AAA | CCA | GAA | GGC | CTG | CTG | ACA | CAA | AAC | GAA | GAA | CTG | 1292 |
| Glu | Glu | Leu | Pro | Lys | Pro | Glu | Gly | Leu | Leu | Thr | Gln | Asn | Glu | Glu | Leu | |
| | | | 340 | | | | | 345 | | | | | 350 | | | |
| TGG | GAA | CCG | CTC | TAC | GCT | TGC | TAC | CAG | TCA | CTT | CAG | GCG | TGT | GGC | ATG | 1340 |
| Trp | Glu | Pro | Leu | Tyr | Ala | Cys | Tyr | Gln | Ser | Leu | Gln | Ala | Cys | Gly | Met | |
| | | 355 | | | | | 360 | | | | | 365 | | | | |
| GGT | ATT | ATC | GCC | AAC | GGC | GAT | CTG | CTC | GAC | ACC | CTG | CGC | CGC | GTG | AAA | 1388 |
| Gly | Ile | Ile | Ala | Asn | Gly | Asp | Leu | Leu | Asp | Thr | Leu | Arg | Arg | Val | Lys | |
| | 370 | | | | | 375 | | | | | 380 | | | | | |
| TGT | TTC | GGC | GTA | CCG | CTG | GTC | CGT | ATT | GAT | ATC | CGT | CAG | GAG | AGC | ACG | 1436 |
| Cys | Phe | Gly | Val | Pro | Leu | Val | Arg | Ile | Asp | Ile | Arg | Gln | Glu | Ser | Thr | |
| 385 | | | | | 390 | | | | | 395 | | | | | 400 | |
| CGT | CAT | ACC | GAA | GCG | CTG | GGC | GAG | CTG | ACC | CGC | TAC | CTC | GGT | ATC | GGC | 1484 |
| Arg | His | Thr | Glu | Ala | Leu | Gly | Glu | Leu | Thr | Arg | Tyr | Leu | Gly | Ile | Gly | |
| | | | | 405 | | | | | 410 | | | | | 415 | | |
| GAC | TAC | GAA | AGC | TGG | TCA | GAG | GCC | GAC | AAA | CAG | GCG | TTC | CTG | ATC | CGC | 1532 |
| Asp | Tyr | Glu | Ser | Trp | Ser | Glu | Ala | Asp | Lys | Gln | Ala | Phe | Leu | Ile | Arg | |
| | | | 420 | | | | | 425 | | | | | 430 | | | |
| GAA | CTG | AAC | TCC | AAA | CGT | CCG | CTT | CTG | CCG | CGC | AAC | TGG | CAA | CCA | AGC | 1580 |
| Glu | Leu | Asn | Ser | Lys | Arg | Pro | Leu | Leu | Pro | Arg | Asn | Trp | Gln | Pro | Ser | |
| | | 435 | | | | | 440 | | | | | 445 | | | | |
| GCC | GAA | ACG | CGC | GAA | GTG | CTC | GAT | ACC | TGC | CAG | GTG | ATT | GCC | GAA | GCA | 1628 |
| Ala | Glu | Thr | Arg | Glu | Val | Leu | Asp | Thr | Cys | Gln | Val | Ile | Ala | Glu | Ala | |
| | 450 | | | | | 455 | | | | | 460 | | | | | |
| CCG | CAA | GGC | TCC | ATT | GCC | GCC | TAC | GTG | ATC | TCG | ATG | GCG | AAA | ACG | CCG | 1676 |
| Pro | Gln | Gly | Ser | Ile | Ala | Ala | Tyr | Val | Ile | Ser | Met | Ala | Lys | Thr | Pro | |
| 465 | | | | | 470 | | | | | 475 | | | | | 480 | |
| TCC | GAC | GTA | CTG | GCT | GTC | CAC | CTG | CTG | CTG | AAA | GAA | GCG | GGT | ATC | GGG | 1724 |
| Ser | Asp | Val | Leu | Ala | Val | His | Leu | Leu | Leu | Lys | Glu | Ala | Gly | Ile | Gly | |
| | | | | 485 | | | | | 490 | | | | | 495 | | |

| | | | | | | | | | | | | | | | | |
|---|---|---|---|---|---|---|---|---|---|---|---|---|---|---|---|---|
| TTT | GCG | ATG | CCG | GTT | GCT | CCG | CTG | TTT | GAA | ACC | CTC | GAT | GAT | CTG | AAC | 1772 |
| Phe | Ala | Met | Pro | Val | Ala | Pro | Leu | Phe | Glu | Thr | Leu | Asp | Asp | Leu | Asn | |
| | | 500 | | | | | 505 | | | | | 510 | | | | |
| AAC | GCC | AAC | GAT | GTC | ATG | ACC | CAG | CTG | CTC | AAT | ATT | GAC | TGG | TAT | CGT | 1820 |
| Asn | Ala | Asn | Asp | Val | Met | Thr | Gln | Leu | Leu | Asn | Ile | Asp | Trp | Tyr | Arg | |
| | | 515 | | | | | 520 | | | | | 525 | | | | |
| GGC | CTG | ATT | CAG | GGC | AAA | CAG | ATG | GTG | ATG | ATT | GGC | TAT | TCC | GAC | TCA | 1868 |
| Gly | Leu | Ile | Gln | Gly | Lys | Gln | Met | Val | Met | Ile | Gly | Tyr | Ser | Asp | Ser | |
| 530 | | | | | 535 | | | | | 540 | | | | | | |
| GCA | AAA | GAT | GCG | GGA | GTG | ATG | GCA | GCT | TCC | TGG | GCG | CAA | TAT | CAG | GCA | 1916 |
| Ala | Lys | Asp | Ala | Gly | Val | Met | Ala | Ala | Ser | Trp | Ala | Gln | Tyr | Gln | Ala | |
| 545 | | | | | 550 | | | | | 555 | | | | | 560 | |
| CAG | GAT | GCA | TTA | ATC | AAA | ACC | TGC | GAA | AAA | GCG | GGT | ATT | GAG | CTG | ACG | 1964 |
| Gln | Asp | Ala | Leu | Ile | Lys | Thr | Cys | Glu | Lys | Ala | Gly | Ile | Glu | Leu | Thr | |
| | | | | 565 | | | | | 570 | | | | | 575 | | |
| TTG | TTC | CAC | GGT | CGC | GGC | GGT | TCC | ATT | GGT | CGC | GGC | GGC | GCA | CCT | GCT | 2012 |
| Leu | Phe | His | Gly | Arg | Gly | Gly | Ser | Ile | Gly | Arg | Gly | Gly | Ala | Pro | Ala | |
| | | | 580 | | | | | 585 | | | | | 590 | | | |
| CAT | GCG | GCG | CTG | CTG | TCA | CAA | CCG | CCA | GGA | AGC | CTG | AAA | GGC | GGC | CTG | 2060 |
| His | Ala | Ala | Leu | Leu | Ser | Gln | Pro | Pro | Gly | Ser | Leu | Lys | Gly | Gly | Leu | |
| | 595 | | | | | 600 | | | | | 605 | | | | | |
| CGC | GTA | ACC | GAA | CAG | GGC | GAG | ATG | ATC | CGC | TTT | AAA | TAT | GGT | CTG | CCA | 2108 |
| Arg | Val | Thr | Glu | Gln | Gly | Glu | Met | Ile | Arg | Phe | Lys | Tyr | Gly | Leu | Pro | |
| | 610 | | | | | 615 | | | | | 620 | | | | | |
| GAA | ATC | ACC | GTC | AGC | AGC | CTG | TCG | CTT | TAT | ACC | GGG | GCG | ATT | CTG | GAA | 2156 |
| Glu | Ile | Thr | Val | Ser | Ser | Leu | Ser | Leu | Tyr | Thr | Gly | Ala | Ile | Leu | Glu | |
| 625 | | | | | 630 | | | | | 635 | | | | | 640 | |
| GCC | AAC | CTG | CTG | CCA | CCG | CCG | GAG | CCG | AAA | GAG | AGC | TGG | CGT | CGC | ATT | 2204 |
| Ala | Asn | Leu | Leu | Pro | Pro | Pro | Glu | Pro | Lys | Glu | Ser | Trp | Arg | Arg | Ile | |
| | | | | 645 | | | | | 650 | | | | | 655 | | |
| ATG | GAT | GAA | CTG | TCA | GTC | ATC | TCC | TGC | GAT | GTC | TAC | CGC | GGC | TAC | GTA | 2252 |
| Met | Asp | Glu | Leu | Ser | Val | Ile | Ser | Cys | Asp | Val | Tyr | Arg | Gly | Tyr | Val | |
| | | | 660 | | | | | 665 | | | | | 670 | | | |
| CGT | GAA | AAC | AAA | GAT | TTT | GTG | CCT | TAC | TTC | CGC | TCC | GCT | ACG | CCG | GAA | 2300 |
| Arg | Glu | Asn | Lys | Asp | Phe | Val | Pro | Tyr | Phe | Arg | Ser | Ala | Thr | Pro | Glu | |
| | | 675 | | | | | 680 | | | | | 685 | | | | |
| CAA | GAA | CTG | GGC | AAA | CTG | CCG | TTG | GGT | TCA | CGT | CCG | GCG | AAA | CGT | CGC | 2348 |
| Gln | Glu | Leu | Gly | Lys | Leu | Pro | Leu | Gly | Ser | Arg | Pro | Ala | Lys | Arg | Arg | |
| | 690 | | | | | 695 | | | | | 700 | | | | | |
| CCA | ACC | GGC | GGC | GTC | GAG | TCA | CTA | CGC | GCC | ATT | CCG | TGG | ATC | TTC | GCC | 2396 |
| Pro | Thr | Gly | Gly | Val | Glu | Ser | Leu | Arg | Ala | Ile | Pro | Trp | Ile | Phe | Ala | |
| 705 | | | | | 710 | | | | | 715 | | | | | 720 | |
| TGG | ACG | CAA | AAC | CGT | CTG | ATG | CTC | CCC | GCC | TGG | CTG | GGT | GCA | GGT | ACG | 2444 |
| Trp | Thr | Gln | Asn | Arg | Leu | Met | Leu | Pro | Ala | Trp | Leu | Gly | Ala | Gly | Thr | |
| | | | | 725 | | | | | 730 | | | | | 735 | | |
| GCG | CTG | CAA | AAA | GTG | GTC | GAA | GAC | GGC | AAA | CAG | AGC | GAG | CTG | GAG | GCT | 2492 |
| Ala | Leu | Gln | Lys | Val | Val | Glu | Asp | Gly | Lys | Gln | Ser | Glu | Leu | Glu | Ala | |
| | | | 740 | | | | | 745 | | | | | 750 | | | |
| ATG | TGC | CGC | GAT | TGG | CCA | TTC | TTC | TCG | ACG | CGT | CTC | GGC | ATG | CTG | GAG | 2540 |
| Met | Cys | Arg | Asp | Trp | Pro | Phe | Phe | Ser | Thr | Arg | Leu | Gly | Met | Leu | Glu | |
| | | 755 | | | | | 760 | | | | | 765 | | | | |
| ATG | GTC | TTC | GCC | AAA | GCA | GAC | CTG | TGG | CTG | GCG | GAA | TAC | TAT | GAC | CAA | 2588 |
| Met | Val | Phe | Ala | Lys | Ala | Asp | Leu | Trp | Leu | Ala | Glu | Tyr | Tyr | Asp | Gln | |
| | 770 | | | | | 775 | | | | | 780 | | | | | |
| CGC | CTG | GTA | GAC | AAA | GCA | CTG | TGG | CCG | TTA | GGT | AAA | GAG | TTA | CGC | AAC | 2636 |
| Arg | Leu | Val | Asp | Lys | Ala | Leu | Trp | Pro | Leu | Gly | Lys | Glu | Leu | Arg | Asn | |
| 785 | | | | | 790 | | | | | 795 | | | | | 800 | |
| CTG | CAA | GAA | GAA | GAC | ATC | AAA | GTG | GTG | CTG | GCG | ATT | GCC | AAC | GAT | TCC | 2684 |
| Leu | Gln | Glu | Glu | Asp | Ile | Lys | Val | Val | Leu | Ala | Ile | Ala | Asn | Asp | Ser | |
| | | | | 805 | | | | | 810 | | | | | 815 | | |

```
CAT CTG ATG GCC GAT CTG CCG TGG ATT GCA GAG TCT ATT CAG CTA CGG      2732
His Leu Met Ala Asp Leu Pro Trp Ile Ala Glu Ser Ile Gln Leu Arg
        820                 825                 830

AAT ATT TAC ACC GAC CCG CTG AAC GTA TTG CAG GCC GAG TTG CTG CAC      2780
Asn Ile Tyr Thr Asp Pro Leu Asn Val Leu Gln Ala Glu Leu Leu His
        835                 840                 845

CGC TCC CGC CAG GCA GAA AAA GAA GGC CAG GAA CCG GAT CCT CGC GTC      2828
Arg Ser Arg Gln Ala Glu Lys Glu Gly Gln Glu Pro Asp Pro Arg Val
850                 855                 860

GAA CAA GCG TTA ATG GTC ACT ATT GCC GGG ATT GCG GCA GGT ATG CGT      2876
Glu Gln Ala Leu Met Val Thr Ile Ala Gly Ile Ala Ala Gly Met Arg
865                 870                 875                 880

AAT ACC GGC TAA TCTTCCTCTT CTGCAAACCC TCGTGCTTTT GCGCGAGGGT          2928
Asn Thr Gly

TTTCTGAAAT ACTTCTGTTC AACACCCTC  GTTTTCAATA TATTTCTGTC TGCATTTTAT    2988
TCAAATTCTG AATATACCTT CAGATATCCT TAAGGGCCTC GTGATACGCC TATTTTTATA    3048
GGTTAATGTC ATGATAATAA TGGTTTCTTA GACGTCAGGT GGCACTTTTC GGGGAAATGT    3108
GCGCGGAACC CCTATTTGTT TATTTTTCTA AATACATTCA AATATGTATC CGCTCATGAG    3168
ACAATAACCC TGATAAATGC TTCAATAATA TTGAAAAAGG AAGAGTATGA GTATTCAACA    3228
TTTCCGTGTC GCCCTTATTC CCTTTTTTGC GGCATTTTGC CTTCCTGTTT TGCTCACCC    3288
AGAAACGCTG GTGAAAGTAA AAGATGCTGA AGATCAGTTG GGTGCACGAG TGGGTTACAT    3348
CGAACTGGAT CTCAACAGCG GTAAGATCCT TGAGAGTTTT CGCCCCGAAG AACGTTTTCC    3408
AATGATGAGC ACTTTTAAAG TTCTGCTATG TGGCGCGGTA TTATCCCGTA TTGACGCCGG    3468
GCAAGAGCAA CTCGGTCGCC GCATACACTA TTCTCAGAAT GACTTGGTTG AGTACTCACC    3528
AGTCACAGAA AAGCATCTTA CGGATGGCAT GACAGTAAGA GAATTATGCA GTGCTGCCAT    3588
AACCATGAGT GATAACACTG CGGCCAACTT ACTTCTGACA ACGATCGGAG GACCGAAGGA    3648
GCTAACCGCT TTTTTGCACA ACATGGGGGA TCATGTAACT CGCCTTGATC GTTGGGAACC    3708
GGAGCTGAAT GAAGCCATAC CAAACGACGA GCGTGACACC ACGATGCCTG TAGCAATGGC    3768
AACAACGTTG CGCAAACTAT TAACTGGCGA ACTACTTACT CTAGCTTCCC GGCAACAATT    3828
AATAGACTGG ATGGAGGCGG ATAAAGTTGC AGGACCACTT CTGCGCTCGG CCCTTCCGGC    3888
TGGCTGGTTT ATTGCTGATA AATCTGGAGC CGGTGAGCGT GGGTCTCGCG GTATCATTGC    3948
AGCACTGGGG CCAGATGGTA AGCCCTCCCG TATCGTAGTT ATCTACACGA CGGGGAGTCA    4008
GGCAACTATG GATGAACGAA ATAGACAGAT CGCTGAGATA GGTGCCTCAC TGATTAAGCA    4068
TTGGTAACTG TCAGACCAAG TTTACTCATA TATACTTTAG ATTGATTTAA AACTTCATTT    4128
TTAATTTAAA AGGATCTAGG TGAAGATCCT TTTTGATAAT CTCATGACCA AAATCCCTTA    4188
ACGTGAGTTT TCGTTCCACT GAGCGTCAGA CCCCGTAGAA AAGATCAAAG GATCTTCTTG    4248
AGATCCTTTT TTTCTGCGCG TAATCTGCTG CTTGCAAACA AAAAAACCAC CGCTACCAGC    4308
GGTGGTTTGT TTGCCGGATC AAGAGCTACC AACTCTTTTT CCGAAGGTAA CTGGCTTCAG    4368
CAGAGCGCAG ATACCAAATA CTGTCCTTCT AGTGTAGCCG TAGTTAGGCC ACCACTTCAA    4428
GAACTCTGTA GCACCGCCTA CATACCTCGC TCTGCTAATC CTGTTACCAG TGGCTGCTGC    4488
CAGTGGCGAT AAGTCGTGTC TTACCGGGTT GGACTCAAGA CGATAGTTAC CGGATAAGGC    4548
GCAGCGGTCG GGCTGAACGG GGGGTTCGTG CACACAGCCC AGCTTGGAGC GAACGACCTA    4608
CACCGAACTG AGATACCTAC AGCGTGAGCA TTGAGAAAGC GCCACGCTTC CCGAAGGGAG    4668
AAAGGCGGAC AGGTATCCGG TAAGCGGCAG GGTCGGAACA GGAGAGCGCA CGAGGGAGCT    4728
```

| | | | | |
|---|---|---|---|---|
| TCCAGGGGGA | AACGCCTGGT | ATCTTTATAG | TCCTGTCGGG | TTTCGCCACC | TCTGACTTGA | 4788 |
| GCGTCGATTT | TTGTGATGCT | CGTCAGGGGG | GCGGAGCCTA | TGGAAAAACG | CCAGCAACGC | 4848 |
| GGCCTTTTTA | CGGTTCCTGG | CCTTTTGCTG | GCCTTTTGCT | CACATGTTCT | TTCCTGCGTT | 4908 |
| ATCCCCTGAT | TCTGTGGATA | ACCGTATTAC | CGCCTTTGAG | TGAGCTGATA | CCGCTCGCCG | 4968 |
| CAGCCGAACG | ACCGAGCGCA | GCGAGTCAGT | GAGCGAGGAA | GCGGAAGAGC | GCCCAATACG | 5028 |
| CAAACCGCCT | CTCCCCGCGC | GTTGGCCGAT | TCATTAATGC | AGAAGGGTTG | GTTTGCGCAT | 5088 |
| TCACAGTTCT | CCGCAAGAAT | TGATTGGCTC | CAATTCTTGG | AGTGGTGAAT | CCGTTAGCGA | 5148 |
| GGTGCCGCCG | GCTTCCATTC | AGGTCGAGGT | GGCCCGGG | | | 5186 |

(2) INFORMATION FOR SEQ ID NO:2:

(i) SEQUENCE CHARACTERISTICS:
        (A) LENGTH: 883 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Asn  Glu  Gln  Tyr  Ser  Ala  Leu  Arg  Ser  Asn  Val  Ser  Met  Leu  Gly
 1                  5                      10                     15

Lys  Val  Leu  Gly  Glu  Thr  Ile  Lys  Asp  Ala  Leu  Gly  Glu  His  Ile  Leu
                20                      25                     30

Glu  Arg  Val  Glu  Thr  Ile  Arg  Lys  Leu  Ser  Lys  Ser  Ser  Arg  Ala  Gly
            35                      40                     45

Asn  Asp  Ala  Asn  Arg  Gln  Glu  Leu  Leu  Thr  Thr  Leu  Gln  Asn  Leu  Ser
        50                      55                     60

Asn  Asp  Glu  Leu  Leu  Pro  Val  Ala  Arg  Ala  Phe  Ser  Gln  Phe  Leu  Asn
65                      70                      75                         80

Leu  Ala  Asn  Thr  Ala  Glu  Gln  Tyr  His  Ser  Ile  Ser  Pro  Lys  Gly  Glu
                85                      90                     95

Ala  Ala  Ser  Asn  Pro  Glu  Val  Ile  Ala  Arg  Thr  Leu  Arg  Lys  Leu  Lys
               100                     105                    110

Asn  Gln  Pro  Glu  Leu  Ser  Glu  Asp  Thr  Ile  Lys  Lys  Ala  Val  Glu  Ser
           115                     120                    125

Leu  Ser  Leu  Glu  Leu  Val  Leu  Thr  Ala  His  Pro  Thr  Glu  Ile  Thr  Arg
       130                     135                    140

Arg  Thr  Leu  Ile  His  Lys  Met  Val  Glu  Val  Asn  Ala  Cys  Leu  Lys  Gln
145                     150                     155                        160

Leu  Asp  Asn  Lys  Asp  Ile  Ala  Asp  Tyr  Glu  His  Asn  Gln  Leu  Met  Arg
               165                     170                    175

Arg  Leu  Arg  Gln  Leu  Ile  Ala  Gln  Ser  Trp  His  Thr  Asp  Glu  Ile  Arg
           180                     185                    190

Lys  Leu  Arg  Pro  Ser  Pro  Val  Asp  Glu  Ala  Lys  Trp  Gly  Phe  Ala  Val
       195                     200                    205

Val  Glu  Asn  Ser  Leu  Trp  Gln  Gly  Val  Pro  Asn  Tyr  Leu  Arg  Glu  Leu
   210                     215                    220

Asn  Glu  Gln  Leu  Glu  Glu  Asn  Leu  Gly  Tyr  Lys  Leu  Pro  Val  Glu  Phe
225                     230                     235                        240

Val  Pro  Val  Arg  Phe  Thr  Ser  Trp  Met  Gly  Gly  Asp  Arg  Asp  Gly  Asn
               245                     250                    255

Pro  Asn  Val  Thr  Ala  Asp  Ile  Thr  Arg  His  Val  Leu  Leu  Leu  Ser  Arg
           260                     265                    270

Trp  Lys  Ala  Thr  Asp  Leu  Phe  Leu  Lys  Asp  Ile  Gln  Val  Leu  Val  Ser
```

|   |   |   |   |   | 275 |   |   |   |   | 280 |   |   |   |   | 285 |   |   |
|---|---|---|---|---|---|---|---|---|---|---|---|---|---|---|---|---|---|
| Glu | Leu 290 | Ser | Met | Val | Glu | Ala 295 | Thr | Pro | Glu | Leu 300 | Leu | Ala | Leu | Val | Gly |
| Glu 305 | Glu | Gly | Ala | Ala 310 | Glu | Pro | Tyr | Arg | Tyr 315 | Leu | Met | Lys | Asn | Leu | Arg 320 |
| Ser | Arg | Leu | Met | Ala 325 | Thr | Gln | Ala | Trp | Leu 330 | Glu | Ala | Arg | Leu | Lys 335 | Gly |
| Glu | Glu | Leu | Pro 340 | Lys | Pro | Glu | Gly | Leu 345 | Leu | Thr | Gln | Asn | Glu 350 | Glu | Leu |
| Trp | Glu | Pro 355 | Leu | Tyr | Ala | Cys | Tyr 360 | Gln | Ser | Leu | Gln | Ala 365 | Cys | Gly | Met |
| Gly | Ile 370 | Ile | Ala | Asn | Gly | Asp 375 | Leu | Leu | Asp | Thr | Leu 380 | Arg | Arg | Val | Lys |
| Cys 385 | Phe | Gly | Val | Pro | Leu 390 | Val | Arg | Ile | Asp | Ile 395 | Arg | Gln | Glu | Ser | Thr 400 |
| Arg | His | Thr | Glu | Ala 405 | Leu | Gly | Glu | Leu | Thr 410 | Arg | Tyr | Leu | Gly | Ile 415 | Gly |
| Asp | Tyr | Glu | Ser 420 | Trp | Ser | Glu | Ala | Asp 425 | Lys | Gln | Ala | Phe | Leu 430 | Ile | Arg |
| Glu | Leu | Asn 435 | Ser | Lys | Arg | Pro | Leu 440 | Leu | Pro | Arg | Asn | Trp 445 | Gln | Pro | Ser |
| Ala | Glu 450 | Thr | Arg | Glu | Val | Leu 455 | Asp | Thr | Cys | Gln | Val 460 | Ile | Ala | Glu | Ala |
| Pro 465 | Gln | Gly | Ser | Ile | Ala 470 | Ala | Tyr | Val | Ile | Ser 475 | Met | Ala | Lys | Thr | Pro 480 |
| Ser | Asp | Val | Leu | Ala 485 | Val | His | Leu | Leu | Leu 490 | Lys | Glu | Ala | Gly | Ile 495 | Gly |
| Phe | Ala | Met | Pro 500 | Val | Ala | Pro | Leu | Phe 505 | Glu | Thr | Leu | Asp | Asp 510 | Leu | Asn |
| Asn | Ala | Asn 515 | Asp | Val | Met | Thr | Gln 520 | Leu | Leu | Asn | Ile | Asp 525 | Trp | Tyr | Arg |
| Gly | Leu 530 | Ile | Gln | Gly | Lys | Gln 535 | Met | Val | Met | Ile | Gly 540 | Tyr | Ser | Asp | Ser |
| Ala 545 | Lys | Asp | Ala | Gly | Val 550 | Met | Ala | Ala | Ser | Trp 555 | Ala | Gln | Tyr | Gln | Ala 560 |
| Gln | Asp | Ala | Leu | Ile 565 | Lys | Thr | Cys | Glu | Lys 570 | Ala | Gly | Ile | Glu | Leu 575 | Thr |
| Leu | Phe | His | Gly 580 | Arg | Gly | Gly | Ser | Ile 585 | Gly | Arg | Gly | Gly | Ala 590 | Pro | Ala |
| His | Ala | Ala 595 | Leu | Leu | Ser | Gln | Pro 600 | Pro | Gly | Ser | Leu | Lys 605 | Gly | Gly | Leu |
| Arg | Val 610 | Thr | Glu | Gln | Gly | Glu 615 | Met | Ile | Arg | Phe | Lys 620 | Tyr | Gly | Leu | Pro |
| Glu 625 | Ile | Thr | Val | Ser | Ser 630 | Leu | Ser | Leu | Tyr | Thr 635 | Gly | Ala | Ile | Leu | Glu 640 |
| Ala | Asn | Leu | Leu | Pro 645 | Pro | Pro | Glu | Pro | Lys 650 | Glu | Ser | Trp | Arg | Arg 655 | Ile |
| Met | Asp | Glu | Leu 660 | Ser | Val | Ile | Ser | Cys 665 | Asp | Val | Tyr | Arg | Gly 670 | Tyr | Val |
| Arg | Glu | Asn 675 | Lys | Asp | Phe | Val | Pro 680 | Tyr | Phe | Arg | Ser | Ala 685 | Thr | Pro | Glu |
| Gln | Glu 690 | Leu | Gly | Lys | Leu | Pro 695 | Leu | Gly | Ser | Arg | Pro 700 | Ala | Lys | Arg | Arg |

| | | | | | | | | | | | | | | | |
|---|---|---|---|---|---|---|---|---|---|---|---|---|---|---|---|
| Pro | Thr | Gly | Gly | Val | Glu | Ser | Leu | Arg | Ala | Ile | Pro | Trp | Ile | Phe | Ala |
| 705 | | | | | 710 | | | | | 715 | | | | | 720 |
| Trp | Thr | Gln | Asn | Arg | Leu | Met | Leu | Pro | Ala | Trp | Leu | Gly | Ala | Gly | Thr |
| | | | | 725 | | | | | 730 | | | | | 735 | |
| Ala | Leu | Gln | Lys | Val | Val | Glu | Asp | Gly | Lys | Gln | Ser | Glu | Leu | Glu | Ala |
| | | | 740 | | | | | 745 | | | | | 750 | | |
| Met | Cys | Arg | Asp | Trp | Pro | Phe | Phe | Ser | Thr | Arg | Leu | Gly | Met | Leu | Glu |
| | | 755 | | | | | 760 | | | | | 765 | | | |
| Met | Val | Phe | Ala | Lys | Ala | Asp | Leu | Trp | Leu | Ala | Glu | Tyr | Tyr | Asp | Gln |
| | 770 | | | | | 775 | | | | | 780 | | | | |
| Arg | Leu | Val | Asp | Lys | Ala | Leu | Trp | Pro | Leu | Gly | Lys | Glu | Leu | Arg | Asn |
| 785 | | | | | 790 | | | | | 795 | | | | | 800 |
| Leu | Gln | Glu | Glu | Asp | Ile | Lys | Val | Val | Leu | Ala | Ile | Ala | Asn | Asp | Ser |
| | | | | 805 | | | | | 810 | | | | | 815 | |
| His | Leu | Met | Ala | Asp | Leu | Pro | Trp | Ile | Ala | Glu | Ser | Ile | Gln | Leu | Arg |
| | | | 820 | | | | | 825 | | | | | 830 | | |
| Asn | Ile | Tyr | Thr | Asp | Pro | Leu | Asn | Val | Leu | Gln | Ala | Glu | Leu | Leu | His |
| | | 835 | | | | | 840 | | | | | 845 | | | |
| Arg | Ser | Arg | Gln | Ala | Glu | Lys | Glu | Gly | Gln | Glu | Pro | Asp | Pro | Arg | Val |
| | 850 | | | | | 855 | | | | | 860 | | | | |
| Glu | Gln | Ala | Leu | Met | Val | Thr | Ile | Ala | Gly | Ile | Ala | Ala | Gly | Met | Arg |
| 865 | | | | | 870 | | | | | 875 | | | | | 880 |
| Asn | Thr | Gly | | | | | | | | | | | | | |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( x i ) SEQUENCE DESCRIPTION: SEQ ID NO:3:

TCGCGAAGTA GCACCTGTCA CTT        23

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( x i ) SEQUENCE DESCRIPTION: SEQ ID NO:4:

ACGGAATTCA ATCTTACGGC C        21

( 2 ) INFORMATION FOR SEQ ID NO:5:

( i ) SEQUENCE CHARACTERISTICS:
        ( A ) LENGTH: 1643 base pairs
        ( B ) TYPE: nucleic acid
        ( C ) STRANDEDNESS: double
        ( D ) TOPOLOGY: linear -continued (i i) MOLECULE TYPE: DNA (genomic)

(v i) ORIGINAL SOURCE:
(A) ORGANISM: Corynebacterium glutamicum
(B) STRAIN: ATCC13869

(i x) FEATURE:
(A) NAME/KEY: mat_peptide
(B) LOCATION: 217..1482

(x i) SEQUENCE DESCRIPTION: SEQ ID NO:5:

```
TCGCGAAGTA GCACCTGTCA CTTTTGTCTC AAATATTAAA TCGAATATCA ATATACGGTC    60

TGTTTATTGG AACGCATCCC AGTGGCTGAG ACGCATCCGC TAAAGCCCCA GGAACCCTGT   120

GCAGAAAGAA AACACTCCTC TGGCTAGGTA GACACAGTTT ATAAAGGTAG AGTTGAGCGG   180

GTAACTGTCA GCACGTAGAT CGAAAGGTGC ACAAAG GTG GCC CTG GTC GTA CAG    234
                                         Met Ala Leu Val Val Gln
                                         1                       5

AAA TAT GGC GGT TCC TCG CTT GAG AGT GCG GAA CGC ATT AGA AAC GTC    282
Lys Tyr Gly Gly Ser Ser Leu Glu Ser Ala Glu Arg Ile Arg Asn Val
            10                  15                  20

GCT GAA CGG ATC GTT GCC ACC AAG AAG GCT GGA AAT GAT GTC GTG GTT    330
Ala Glu Arg Ile Val Ala Thr Lys Lys Ala Gly Asn Asp Val Val Val
        25                  30                  35

GTC TGC TCC GCA ATG GGA GAC ACC ACG GAT GAA CTT CTA GAA CTT GCA    378
Val Cys Ser Ala Met Gly Asp Thr Thr Asp Glu Leu Leu Glu Leu Ala
    40                  45                  50

GCG GCA GTG AAT CCC GTT CCG CCA GCT CGT GAA ATG GAT ATG CTC CTG    426
Ala Ala Val Asn Pro Val Pro Pro Ala Arg Glu Met Asp Met Leu Leu
55                  60                  65                  70

ACT GCT GGT GAG CGT ATT TCT AAC GCT CTC GTC GCC ATG GCT ATT GAG    474
Thr Ala Gly Glu Arg Ile Ser Asn Ala Leu Val Ala Met Ala Ile Glu
                    75                  80                  85

TCC CTT GGC GCA GAA GCT CAA TCT TTC ACT GGC TCT CAG GCT GGT GTG    522
Ser Leu Gly Ala Glu Ala Gln Ser Phe Thr Gly Ser Gln Ala Gly Val
                90                  95                 100

CTC ACC ACC GAG CGC CAC GGA AAC GCA CGC ATT GTT GAC GTC ACA CCG    570
Leu Thr Thr Glu Arg His Gly Asn Ala Arg Ile Val Asp Val Thr Pro
            105                 110                 115

GGT CGT GTG CGT GAA GCA CTC GAT GAG GGC AAG ATC TGC ATT GTT GCT    618
Gly Arg Val Arg Glu Ala Leu Asp Glu Gly Lys Ile Cys Ile Val Ala
        120                 125                 130

GGT TTT CAG GGT GTT AAT AAA GAA ACC CGC GAT GTC ACC ACG TTG GGT    666
Gly Phe Gln Gly Val Asn Lys Glu Thr Arg Asp Val Thr Thr Leu Gly
135                 140                 145                 150

CGT GGT GGT TCT GAC ACC ACT GCA GTT GCG TTG GCA GCT GCT TTG AAC    714
Arg Gly Gly Ser Asp Thr Thr Ala Val Ala Leu Ala Ala Ala Leu Asn
                    155                 160                 165

GCT GAT GTG TGT GAG ATT TAC TCG GAC GTT GAC GGT GTG TAT ACC GCT    762
Ala Asp Val Cys Glu Ile Tyr Ser Asp Val Asp Gly Val Tyr Thr Ala
                170                 175                 180

GAC CCG CGC ATC GTT CCT AAT GCA CAG AAG CTG GAA AAG CTC AGC TTC    810
Asp Pro Arg Ile Val Pro Asn Ala Gln Lys Leu Glu Lys Leu Ser Phe
            185                 190                 195

GAA GAA ATG CTG GAA CTT GCT GCT GTT GGC TCC AAG ATT TTG GTG CTG    858
Glu Glu Met Leu Glu Leu Ala Ala Val Gly Ser Lys Ile Leu Val Leu
        200                 205                 210

CGC AGT GTT GAA TAC GCT CGT GCA TTC AAT GTG CCA CTT CGC GTA CGC    906
Arg Ser Val Glu Tyr Ala Arg Ala Phe Asn Val Pro Leu Arg Val Arg
215                 220                 225                 230

TCG TCT TAT AGT AAT GAT CCC GGC ACT TTG ATT GCC GGC TCT ATG GAG    954
Ser Ser Tyr Ser Asn Asp Pro Gly Thr Leu Ile Ala Gly Ser Met Glu
```

```
                             235                          240                           245
GAT  ATT  CCT  GTG  GAA  GAA  GCA  GTC  CTT  ACC  GGT  GTC  GCA  ACC  GAC  AAG        1002
Asp  Ile  Pro  Val  Glu  Glu  Ala  Val  Leu  Thr  Gly  Val  Ala  Thr  Asp  Lys
               250                      255                      260

TCC  GAA  GCC  AAA  GTA  ACC  GTT  CTG  GGT  ATT  TCC  GAT  AAG  CCA  GGC  GAG        1050
Ser  Glu  Ala  Lys  Val  Thr  Val  Leu  Gly  Ile  Ser  Asp  Lys  Pro  Gly  Glu
               265                      270                      275

GCT  GCC  AAG  GTT  TTC  CGT  GCG  TTG  GCT  GAT  GCA  GAA  ATC  AAC  ATT  GAC        1098
Ala  Ala  Lys  Val  Phe  Arg  Ala  Leu  Ala  Asp  Ala  Glu  Ile  Asn  Ile  Asp
               280                      285                      290

ATG  GTT  CTG  CAG  AAC  GTC  TCC  TCT  GTG  GAA  GAC  GGC  ACC  ACC  GAC  ATC        1146
Met  Val  Leu  Gln  Asn  Val  Ser  Ser  Val  Glu  Asp  Gly  Thr  Thr  Asp  Ile
295                      300                      305                      310

ACG  TTC  ACC  TGC  CCT  CGC  GCT  GAC  GGA  CGC  CGT  GCG  ATG  GAG  ATC  TTG        1194
Thr  Phe  Thr  Cys  Pro  Arg  Ala  Asp  Gly  Arg  Arg  Ala  Met  Glu  Ile  Leu
               315                      320                      325

AAG  AAG  CTT  CAG  GTT  CAG  GGC  AAC  TGG  ACC  AAT  GTG  CTT  TAC  GAC  GAC        1242
Lys  Lys  Leu  Gln  Val  Gln  Gly  Asn  Trp  Thr  Asn  Val  Leu  Tyr  Asp  Asp
               330                      335                      340

CAG  GTC  GGC  AAA  GTC  TCC  CTC  GTG  GGT  GCT  GGC  ATG  AAG  TCT  CAC  CCA        1290
Gln  Val  Gly  Lys  Val  Ser  Leu  Val  Gly  Ala  Gly  Met  Lys  Ser  His  Pro
               345                      350                      355

GGT  GTT  ACC  GCA  GAG  TTC  ATG  GAA  GCT  CTG  CGC  GAT  GTC  AAC  GTG  AAC        1338
Gly  Val  Thr  Ala  Glu  Phe  Met  Glu  Ala  Leu  Arg  Asp  Val  Asn  Val  Asn
               360                      365                      370

ATC  GAA  TTG  ATT  TCC  ACC  TCT  GAG  ATC  CGC  ATT  TCC  GTG  CTG  ATC  CGT        1386
Ile  Glu  Leu  Ile  Ser  Thr  Ser  Glu  Ile  Arg  Ile  Ser  Val  Leu  Ile  Arg
375                      380                      385                      390

GAA  GAT  GAT  CTG  GAT  GCT  GCT  GCA  CGT  GCA  TTG  CAT  GAG  CAG  TTC  CAG        1434
Glu  Asp  Asp  Leu  Asp  Ala  Ala  Ala  Arg  Ala  Leu  His  Glu  Gln  Phe  Gln
               395                      400                      405

CTG  GGC  GGC  GAA  GAC  GAA  GCC  GTC  GTT  TAT  GCA  GGC  ACC  GGA  CGC  TAA        1482
Leu  Gly  Gly  Glu  Asp  Glu  Ala  Val  Val  Tyr  Ala  Gly  Thr  Gly  Arg
               410                      415                      420

AGTTTTAAAG  GAGTAGTTTT  ACAATGACCA  CCATCGCAGT  TGTTGGTGCA  ACCGGCCAGG              1542

TCGGCCAGGT  TATGCGCACC  CTTTTGGAAG  AGCGCAATTT  CCCAGCTGAC  ACTGTTCGTT              1602

TCTTTGCTTC  CCCGCGTTCC  GCAGGCCGTA  AGATTGAATT  C                                    1643
```

( 2 ) INFORMATION FOR SEQ ID NO:6:

( i ) SEQUENCE CHARACTERISTICS:
        ( A ) LENGTH: 421 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ala  Leu  Val  Val  Gln  Lys  Tyr  Gly  Gly  Ser  Ser  Leu  Glu  Ser  Ala
1                   5                        10                       15

Glu  Arg  Ile  Arg  Asn  Val  Ala  Glu  Arg  Ile  Val  Ala  Thr  Lys  Lys  Ala
               20                       25                       30

Gly  Asn  Asp  Val  Val  Val  Val  Cys  Ser  Ala  Met  Gly  Asp  Thr  Thr  Asp
               35                       40                       45

Glu  Leu  Leu  Glu  Leu  Ala  Ala  Ala  Val  Asn  Pro  Val  Pro  Pro  Ala  Arg
          50                       55                       60

Glu  Met  Asp  Met  Leu  Leu  Thr  Ala  Gly  Glu  Arg  Ile  Ser  Asn  Ala  Leu
65                       70                       75                       80

Val  Ala  Met  Ala  Ile  Glu  Ser  Leu  Gly  Ala  Glu  Ala  Gln  Ser  Phe  Thr
```

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |

Gly Ser Gln Ala Gly Val Leu Thr Thr Glu Arg His Gly Asn Ala Arg
            100                     105                     110

Ile Val Asp Val Thr Pro Gly Arg Val Arg Glu Ala Leu Asp Glu Gly
            115                     120                     125

Lys Ile Cys Ile Val Ala Gly Phe Gln Gly Val Asn Lys Glu Thr Arg
        130                     135                 140

Asp Val Thr Thr Leu Gly Arg Gly Gly Ser Asp Thr Thr Ala Val Ala
145                     150                 155                     160

Leu Ala Ala Ala Leu Asn Ala Asp Val Cys Glu Ile Tyr Ser Asp Val
                165                     170                 175

Asp Gly Val Tyr Thr Ala Asp Pro Arg Ile Val Pro Asn Ala Gln Lys
            180                     185                     190

Leu Glu Lys Leu Ser Phe Glu Glu Met Leu Glu Leu Ala Ala Val Gly
        195                     200                     205

Ser Lys Ile Leu Val Leu Arg Ser Val Glu Tyr Ala Arg Ala Phe Asn
    210                     215                 220

Val Pro Leu Arg Val Arg Ser Ser Tyr Ser Asn Asp Pro Gly Thr Leu
225                     230                 235                     240

Ile Ala Gly Ser Met Glu Asp Ile Pro Val Glu Glu Ala Val Leu Thr
                245                     250                 255

Gly Val Ala Thr Asp Lys Ser Glu Ala Lys Val Thr Val Leu Gly Ile
            260                     265                     270

Ser Asp Lys Pro Gly Glu Ala Ala Lys Val Phe Arg Ala Leu Ala Asp
        275                     280                 285

Ala Glu Ile Asn Ile Asp Met Val Leu Gln Asn Val Ser Ser Val Glu
290                     295                 300

Asp Gly Thr Thr Asp Ile Thr Phe Thr Cys Pro Arg Ala Asp Gly Arg
305                     310                 315                     320

Arg Ala Met Glu Ile Leu Lys Lys Leu Gln Val Gln Gly Asn Trp Thr
                325                     330                 335

Asn Val Leu Tyr Asp Asp Gln Val Gly Lys Val Ser Leu Val Gly Ala
            340                     345                     350

Gly Met Lys Ser His Pro Gly Val Thr Ala Glu Phe Met Glu Ala Leu
        355                     360                 365

Arg Asp Val Asn Val Asn Ile Glu Leu Ile Ser Thr Ser Glu Ile Arg
    370                     375                 380

Ile Ser Val Leu Ile Arg Glu Asp Asp Leu Asp Ala Ala Ala Arg Ala
385                     390                 395                     400

Leu His Glu Gln Phe Gln Leu Gly Gly Glu Asp Glu Ala Val Val Tyr
                405                     410                 415

Ala Gly Thr Gly Arg
            420

(2) INFORMATION FOR SEQ ID NO:7:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Corynebacterium glutamicum
        (B) STRAIN: ATCC13869

(ix) FEATURE:
    (A) NAME/KEY: mat_peptide
    (B) LOCATION: 964..1482

(xi) SEQUENCE DESCRIPTION: SEQ ID NO:7:

```
TCGCGAAGTA GCACCTGTCA CTTTTGTCTC AAATATTAAA TCGAATATCA ATATACGGTC      60
TGTTTATTGG AACGCATCCC AGTGGCTGAG ACGCATCCGC TAAAGCCCCA GGAACCCTGT     120
GCAGAAAGAA AACACTCCTC TGGCTAGGTA GACACAGTTT ATAAGGTAG  AGTTGAGCGG     180
GTAACTGTCA GCACGTAGAT CGAAAGGTGC ACAAAGGTGG CCCTGGTCGT ACAGAAATAT     240
GGCGGTTCCT CGCTTGAGAG TGCGGAACGC ATTAGAAACG TCGCTGAACG GATCGTTGCC     300
ACCAAGAAGG CTGGAAATGA TGTCGTGGTT GTCTGCTCCG CAATGGGAGA CACCACGGAT     360
GAACTTCTAG AACTTGCAGC GGCAGTGAAT CCCGTTCCGC CAGCTCGTGA AATGGATATG     420
CTCCTGACTG CTGGTGAGCG TATTTCTAAC GCTCTCGTCG CCATGGCTAT TGAGTCCCTT     480
GGCGCAGAAG CTCAATCTTT CACTGGCTCT CAGGCTGGTG TGCTCACCAC CGAGCGCCAC     540
GGAAACGCAC GCATTGTTGA CGTCACACCG GGTCGTGTGC GTGAAGCACT CGATGAGGGC     600
AAGATCTGCA TTGTTGCTGG TTTTCAGGGT GTTAATAAAG AAACCCGCGA TGTCACCACG     660
TTGGGTCGTG GTGGTTCTGA CACCACTGCA GTTGCGTTGG CAGCTGCTTT GAACGCTGAT     720
GTGTGTGAGA TTTACTCGGA CGTTGACGGT GTGTACCG   CTGACCCGCG CATCGTTCCT     780
AATGCACAGA AGCTGGAAAA GCTCAGCTTC GAAGAAATGC TGGAACTTGC TGCTGTTGGC     840
TCCAAGATTT TGGTGCTGCG CAGTGTTGAA TACGCTCGTG CATTCAATGT GCCACTTCGC     900
GTACGCTCGT CTTATAGTAA TGATCCCGGC ACTTTGATTG CCGGCTCTAT GGAGGATATT     960
```

```
CCT GTG GAA GAA GCA GTC CTT ACC GGT GTC GCA ACC GAC AAG TCC GAA      1008
Met Glu Glu Ala Val Leu Thr Gly Val Ala Thr Asp Lys Ser Glu
 1               5                  10                  15

GCC AAA GTA ACC GTT CTG GGT ATT TCC GAT AAG CCA GGC GAG GCT GCC      1056
Ala Lys Val Thr Val Leu Gly Ile Ser Asp Lys Pro Gly Glu Ala Ala
                20                  25                  30

AAG GTT TTC CGT GCG TTG GCT GAT GCA GAA ATC AAC ATT GAC ATG GTT      1104
Lys Val Phe Arg Ala Leu Ala Asp Ala Glu Ile Asn Ile Asp Met Val
            35                  40                  45

CTG CAG AAC GTC TCC TCT GTG GAA GAC GGC ACC ACC GAC ATC ACG TTC      1152
Leu Gln Asn Val Ser Ser Val Glu Asp Gly Thr Thr Asp Ile Thr Phe
        50                  55                  60

ACC TGC CCT CGC GCT GAC GGA CGC CGT GCG ATG GAG ATC TTG AAG AAG      1200
Thr Cys Pro Arg Ala Asp Gly Arg Arg Ala Met Glu Ile Leu Lys Lys
    65                  70                  75

CTT CAG GTT CAG GGC AAC TGG ACC AAT GTG CTT TAC GAC GAC CAG GTC      1248
Leu Gln Val Gln Gly Asn Trp Thr Asn Val Leu Tyr Asp Asp Gln Val
80                  85                  90                  95

GGC AAA GTC TCC CTC GTG GGT GCT GGC ATG AAG TCT CAC CCA GGT GTT      1296
Gly Lys Val Ser Leu Val Gly Ala Gly Met Lys Ser His Pro Gly Val
                100                 105                 110

ACC GCA GAG TTC ATG GAA GCT CTG CGC GAT GTC AAC GTG AAC ATC GAA      1344
Thr Ala Glu Phe Met Glu Ala Leu Arg Asp Val Asn Val Asn Ile Glu
            115                 120                 125

TTG ATT TCC ACC TCT GAG ATC CGC ATT TCC GTG CTG ATC CGT GAA GAT      1392
Leu Ile Ser Thr Ser Glu Ile Arg Ile Ser Val Leu Ile Arg Glu Asp
        130                 135                 140

GAT CTG GAT GCT GCT GCA CGT GCA TTG CAT GAG CAG TTC CAG CTG GGC      1440
Asp Leu Asp Ala Ala Ala Arg Ala Leu His Glu Gln Phe Gln Leu Gly
    145                 150                 155

GGC GAA GAC GAA GCC GTC GTT TAT GCA GGC ACC GGA CGC TAA              1482
Gly Glu Asp Glu Ala Val Val Tyr Ala Gly Thr Gly Arg
```

```
                    160                      165                      170
AGTTTTAAAG    GAGTAGTTTT    ACAATGACCA    CCATCGCAGT    TGTTGGTGCA    ACCGGCCAGG    1542

TCGGCCAGGT    TATGCGCACC    CTTTTGGAAG    AGCGCAATTT    CCCAGCTGAC    ACTGTTCGTT    1602

TCTTTGCTTC    CCCGCGTTCC    GCAGGCCGTA    AGATTGAATT    C                            1643
```

( 2 ) INFORMATION FOR SEQ ID NO:8:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Val  Glu  Glu  Ala  Val  Leu  Thr  Gly  Val  Ala  Thr  Asp  Lys  Ser  Glu  Ala
 1              5                        10                       15

Lys  Val  Thr  Val  Leu  Gly  Ile  Ser  Asp  Lys  Pro  Gly  Glu  Ala  Ala  Lys
              20                       25                       30

Val  Phe  Arg  Ala  Leu  Ala  Asp  Ala  Glu  Ile  Asn  Ile  Asp  Met  Val  Leu
              35                       40                       45

Gln  Asn  Val  Ser  Ser  Val  Glu  Asp  Gly  Thr  Thr  Asp  Ile  Thr  Phe  Thr
         50                       55                       60

Cys  Pro  Arg  Ala  Asp  Gly  Arg  Arg  Ala  Met  Glu  Ile  Leu  Lys  Lys  Leu
65                       70                       75                       80

Gln  Val  Gln  Gly  Asn  Trp  Thr  Asn  Val  Leu  Tyr  Asp  Asp  Gln  Val  Gly
                   85                       90                       95

Lys  Val  Ser  Leu  Val  Gly  Ala  Gly  Met  Lys  Ser  His  Pro  Gly  Val  Thr
              100                      105                      110

Ala  Glu  Phe  Met  Glu  Ala  Leu  Arg  Asp  Val  Asn  Val  Asn  Ile  Glu  Leu
              115                      120                      125

Ile  Ser  Thr  Ser  Glu  Ile  Arg  Ile  Ser  Val  Leu  Ile  Arg  Glu  Asp  Asp
              130                      135                      140

Leu  Asp  Ala  Ala  Ala  Arg  Ala  Leu  His  Glu  Gln  Phe  Gln  Leu  Gly  Gly
145                      150                      155                      160

Glu  Asp  Glu  Ala  Val  Val  Tyr  Ala  Gly  Thr  Gly  Arg
                   165                      170
```

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( x i ) SEQUENCE DESCRIPTION: SEQ ID NO:9:

```
AAAAACCTGC    GTTCTC                                                                16
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: other nucleic acid
                (A) DESCRIPTION: /desc = "Synthetic DNA"

(i i i) HYPOTHETICAL: NO (x i) SEQUENCE DESCRIPTION: SEQ ID NO:10:

TGACTTAAGG TTTACAGGCC                                                                        20

(2) INFORMATION FOR SEQ ID NO:11:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (i i) MOLECULE TYPE: other nucleic acid
                (A) DESCRIPTION: /desc = "Synthetic DNA"

(i i i) HYPOTHETICAL: NO (x i) SEQUENCE DESCRIPTION: SEQ ID NO:11:

ACTGAATTCC AAATGTCCGC                                                                        20

(2) INFORMATION FOR SEQ ID NO:12:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (i i) MOLECULE TYPE: other nucleic acid
                (A) DESCRIPTION: /desc = "Synthetic DNA"

(i i i) HYPOTHETICAL: NO (x i) SEQUENCE DESCRIPTION: SEQ ID NO:12:

AAGTGCAGGC CGTTT                                                                             15